United States Patent
Cohen et al.

(10) Patent No.: US 9,104,791 B2
(45) Date of Patent: Aug. 11, 2015

(54) SYSTEMS AND METHODS FOR EDITING A MODEL OF A PHYSICAL SYSTEM FOR A SIMULATION

(75) Inventors: Robert Cohen, Kensington, MD (US); Mark S. Meents, Germantown, MD (US); Walter E. Ratzat, Silver Spring, MD (US); Kenneth Heyman, Alexandria, VA (US)

(73) Assignee: Immersion Corporation, San Jose, CA (US)

( * ) Notice: Subject to any disclaimer, the term of this patent is extended or adjusted under 35 U.S.C. 154(b) by 542 days.

(21) Appl. No.: 12/473,993

(22) Filed: May 28, 2009

(65) Prior Publication Data

US 2010/0305928 A1 Dec. 2, 2010

(51) Int. Cl.
*G09B 23/28* (2006.01)
*G06F 19/00* (2011.01)
*G09B 23/30* (2006.01)

(52) U.S. Cl.
CPC .......... *G06F 19/3437* (2013.01); *G06F 19/321* (2013.01); *G09B 23/28* (2013.01); *G09B 23/30* (2013.01)

(58) Field of Classification Search
USPC ......... 434/118, 262, 265, 267, 272, 274, 275, 434/283, 365
See application file for complete search history.

(56) References Cited

U.S. PATENT DOCUMENTS

| | | | |
|---|---|---|---|
| 2,524,782 A | 10/1950 | Ferrar et al. | |
| 3,490,059 A | 1/1970 | Paulsen et al. | |
| 3,623,046 A | 11/1971 | Scourtes | |
| 3,875,488 A | 4/1975 | Crocker et al. | |
| 4,050,265 A | 9/1977 | Drennen et al. | |
| 4,103,155 A | 7/1978 | Clark | |
| 4,125,800 A | 11/1978 | Jones | |
| 4,148,014 A | 4/1979 | Burson | |
| 4,311,980 A | 1/1982 | Prudenziati | |
| 4,385,836 A | 5/1983 | Schmitt | |
| 4,391,282 A | 7/1983 | Ando et al. | |

(Continued)

FOREIGN PATENT DOCUMENTS

| | | |
|---|---|---|
| EP | 0 085 518 B1 | 8/1989 |
| EP | 0 470 257 A1 | 2/1992 |

(Continued)

OTHER PUBLICATIONS

Adelstein, B., A Virtual Environment System for the Study of Human Arm Tremor, Submitted to the Dept. of Mechanical Engineering in partial fulfillment of the requirements for the degree of Doctor of Philosophy at the Massachusetts Institute of Technology, Jun. 1989, pp. 1-253.

(Continued)

*Primary Examiner* — Robert J Utama
*Assistant Examiner* — Sadaruz Zaman
(74) *Attorney, Agent, or Firm* — Kilpatrick Townsend Stockton LLP

(57) ABSTRACT

Systems and methods for simulating a medical procedure are disclosed. For example, one described system for simulating a medical procedure includes a physics module configured to model at least one physical property of a user-defined organic object associated with a patient; a display module configured to cause a display of the user-defined organic object; a script module configured to execute a user-defined medical procedure script; a simulation module in communication with the physics module, the display module, and the script module, the simulation module configured to execute a simulation of the medical procedure based at least in part on the user-defined model of the organic object and the user-defined medical procedure script.

35 Claims, 25 Drawing Sheets

(56) References Cited

U.S. PATENT DOCUMENTS

| | | | |
|---|---|---|---|
| 4,400,790 A | 8/1983 | Chambers et al. | |
| 4,443,952 A | 4/1984 | Schulien et al. | |
| 4,546,347 A | 10/1985 | Kirsch | |
| 4,637,264 A | 1/1987 | Takahashi et al. | |
| 4,639,884 A | 1/1987 | Sagues | |
| 4,678,908 A | 7/1987 | LaPlante | |
| 4,680,466 A | 7/1987 | Kuwahara et al. | |
| 4,692,726 A | 9/1987 | Green et al. | |
| 4,695,266 A | 9/1987 | Hui | |
| 4,699,043 A | 10/1987 | Violante De Dionigi | |
| 4,712,101 A | 12/1987 | Culver | |
| 4,724,715 A | 2/1988 | Culver | |
| 4,728,954 A | 3/1988 | Phelan et al. | |
| 4,734,685 A | 3/1988 | Watanabe | |
| 4,776,701 A | 10/1988 | Pettigrew | |
| 4,794,384 A | 12/1988 | Jackson | |
| 4,795,907 A | 1/1989 | Maekawa et al. | |
| 4,799,055 A | 1/1989 | Nestler et al. | |
| 4,803,413 A | 2/1989 | Kendig et al. | |
| 4,811,608 A | 3/1989 | Hilton | |
| 4,815,006 A | 3/1989 | Andersson et al. | |
| 4,819,195 A | 4/1989 | Bell et al. | |
| 4,823,106 A | 4/1989 | Lovell | |
| 4,825,157 A | 4/1989 | Mikan | |
| 4,840,634 A | 6/1989 | Muller et al. | |
| 4,851,771 A | 7/1989 | Ikeda et al. | |
| 4,860,051 A | 8/1989 | Taniguchi et al. | |
| 4,891,889 A | 1/1990 | Tomelleri | |
| 4,906,843 A | 3/1990 | Jones et al. | |
| 4,914,976 A | 4/1990 | Wyllie | |
| 4,935,725 A | 6/1990 | Turnau | |
| 4,935,728 A | 6/1990 | Kley | |
| 4,937,685 A | 6/1990 | Barker et al. | |
| 4,940,234 A | 7/1990 | Ishida et al. | |
| 4,962,448 A | 10/1990 | DeMaio et al. | |
| 4,964,837 A | 10/1990 | Collier | |
| 4,965,446 A | 10/1990 | Vyse | |
| 4,982,504 A | 1/1991 | Soderberg et al. | |
| 5,006,703 A | 4/1991 | Shikunami et al. | |
| 5,024,626 A | 6/1991 | Robbins et al. | |
| 5,053,975 A | 10/1991 | Tsuchihashi et al. | |
| 5,062,830 A | 11/1991 | Dunlap | |
| 5,065,145 A | 11/1991 | Purcell | |
| 5,068,529 A | 11/1991 | Ohno et al. | |
| 5,079,845 A | 1/1992 | Childers | |
| 5,086,197 A | 2/1992 | Liou | |
| 5,095,303 A | 3/1992 | Clark et al. | |
| 5,107,080 A | 4/1992 | Rosen | |
| 5,113,179 A | 5/1992 | Scott-Jackson et al. | |
| 5,116,051 A | 5/1992 | Moncrief et al. | |
| 5,125,261 A | 6/1992 | Powley | |
| 5,132,927 A | 7/1992 | Lenoski et al. | |
| 5,138,154 A | 8/1992 | Hotelling | |
| 5,139,261 A | 8/1992 | Openiano | |
| 5,148,377 A | 9/1992 | McDonald | |
| 5,155,423 A | 10/1992 | Karlen et al. | |
| 5,168,268 A | 12/1992 | Levy | |
| 5,182,557 A | 1/1993 | Lang | |
| 5,195,179 A | 3/1993 | Tokunaga | |
| 5,195,920 A | 3/1993 | Collier | |
| 5,202,961 A | 4/1993 | Mills et al. | |
| 5,204,600 A | 4/1993 | Kahkoska | |
| 5,209,131 A | 5/1993 | Baxter | |
| 5,216,337 A | 6/1993 | Orton et al. | |
| 5,223,658 A | 6/1993 | Suzuki | |
| 5,229,836 A | 7/1993 | Nagano | |
| 5,230,623 A | 7/1993 | Guthrie et al. | |
| 5,235,868 A | 8/1993 | Culver | |
| 5,239,249 A | 8/1993 | Ono | |
| 5,246,316 A | 9/1993 | Smith | |
| 5,247,648 A | 9/1993 | Watkins et al. | |
| 5,254,919 A | 10/1993 | Bridges et al. | |
| 5,275,565 A | 1/1994 | Moncrief | |
| 5,280,276 A | 1/1994 | Kwok | |
| 5,284,330 A | 2/1994 | Carlson et al. | |
| 5,289,273 A | 2/1994 | Lang | |
| 5,296,846 A | 3/1994 | Ledley | |
| 5,313,229 A | 5/1994 | Gilligan et al. | |
| 5,313,230 A | 5/1994 | Venolia et al. | |
| 5,317,336 A | 5/1994 | Hall | |
| 5,329,289 A | 7/1994 | Sakamoto et al. | |
| 5,341,459 A | 8/1994 | Backes | |
| 5,351,692 A | 10/1994 | Dow et al. | |
| 5,359,193 A | 10/1994 | Nyui et al. | |
| 5,374,942 A | 12/1994 | Gilligan et al. | |
| 5,379,663 A | 1/1995 | Hara | |
| 5,384,460 A | 1/1995 | Tseng | |
| 5,385,474 A * | 1/1995 | Brindle | 434/267 |
| 5,390,128 A | 2/1995 | Ryan et al. | |
| 5,390,296 A | 2/1995 | Crandall et al. | |
| 5,396,267 A | 3/1995 | Bouton | |
| 5,397,323 A | 3/1995 | Taylor et al. | |
| 5,398,044 A | 3/1995 | Hill | |
| 5,402,499 A | 3/1995 | Robison et al. | |
| 5,402,582 A | 4/1995 | Raab | |
| 5,402,680 A | 4/1995 | Korenaga | |
| 5,417,696 A | 5/1995 | Kashuba et al. | |
| 5,428,748 A | 6/1995 | Davidson et al. | |
| 5,436,542 A | 7/1995 | Petelin et al. | |
| 5,436,640 A | 7/1995 | Reeves | |
| 5,452,615 A | 9/1995 | Hilton | |
| 5,457,479 A | 10/1995 | Cheng | |
| 5,457,793 A | 10/1995 | Elko et al. | |
| 5,467,763 A | 11/1995 | McMahon et al. | |
| 5,473,344 A | 12/1995 | Bacon et al. | |
| 5,474,082 A | 12/1995 | Junker | |
| 5,481,914 A | 1/1996 | Ward | |
| 5,491,477 A | 2/1996 | Clark et al. | |
| 5,512,919 A | 4/1996 | Araki | |
| 5,514,150 A | 5/1996 | Rostoker | |
| 5,524,195 A | 6/1996 | Clanton, III et al. | |
| 5,526,022 A | 6/1996 | Donahue et al. | |
| 5,530,455 A | 6/1996 | Gillick et al. | |
| 5,543,821 A | 8/1996 | Marchis et al. | |
| 5,547,383 A | 8/1996 | Yamaguchi | |
| 5,550,562 A | 8/1996 | Aoki et al. | |
| 5,550,563 A | 8/1996 | Matheny et al. | |
| 5,570,111 A | 10/1996 | Barrett et al. | |
| 5,576,727 A | 11/1996 | Rosenberg et al. | |
| 5,583,407 A | 12/1996 | Yamaguchi | |
| 5,591,924 A | 1/1997 | Hilton | |
| 5,592,401 A | 1/1997 | Kramer | |
| 5,604,345 A | 2/1997 | Matsuura | |
| 5,611,731 A | 3/1997 | Bouton et al. | |
| 5,623,582 A | 4/1997 | Rosenberg | |
| 5,623,642 A | 4/1997 | Katz et al. | |
| 5,627,531 A | 5/1997 | Posso et al. | |
| 5,628,686 A | 5/1997 | Svancarek et al. | |
| 5,635,897 A | 6/1997 | Kuo | |
| 5,638,421 A | 6/1997 | Serrano et al. | |
| 5,652,603 A | 7/1997 | Abrams | |
| 5,666,138 A | 9/1997 | Culver | |
| 5,680,141 A | 10/1997 | Didomenico et al. | |
| 5,682,886 A * | 11/1997 | Delp et al. | 600/407 |
| 5,691,747 A | 11/1997 | Amano | |
| 5,694,153 A | 12/1997 | Aoyagi et al. | |
| 5,704,791 A * | 1/1998 | Gillio | 434/262 |
| 5,722,071 A | 2/1998 | Berg et al. | |
| 5,724,106 A | 3/1998 | Autry et al. | |
| 5,724,264 A | 3/1998 | Rosenberg et al. | |
| 5,734,108 A | 3/1998 | Walker et al. | |
| 5,740,083 A | 4/1998 | Anderson et al. | |
| 5,745,057 A | 4/1998 | Sasaki et al. | |
| 5,749,577 A | 5/1998 | Couch et al. | |
| 5,755,620 A | 5/1998 | Yamamoto et al. | |
| 5,763,874 A | 6/1998 | Luciano et al. | |
| 5,767,836 A | 6/1998 | Scheffer et al. | |
| 5,771,037 A | 6/1998 | Jackson | |
| 5,795,228 A | 8/1998 | Trumbull et al. | |
| 5,808,568 A | 9/1998 | Wu | |
| 5,808,603 A | 9/1998 | Chen | |
| 5,818,426 A | 10/1998 | Tierney et al. | |
| 5,825,305 A | 10/1998 | Biferno | |
| 5,828,295 A | 10/1998 | Mittel et al. | |

(56) References Cited

U.S. PATENT DOCUMENTS

| | | | |
|---|---|---|---|
| 5,831,593 A | 11/1998 | Rutledge | |
| 5,841,133 A | 11/1998 | Omi | |
| 5,841,423 A | 11/1998 | Carroll, Jr. et al. | |
| 5,841,428 A | 11/1998 | Jaeger et al. | |
| 5,844,673 A | 12/1998 | Ivers | |
| 5,877,748 A | 3/1999 | Redlich | |
| 5,879,327 A | 3/1999 | Moreau DeFarges et al. | |
| 5,889,506 A | 3/1999 | Lopresti et al. | |
| 5,912,661 A | 6/1999 | Siddiqui | |
| 5,917,486 A | 6/1999 | Rylander | |
| 5,919,159 A | 7/1999 | Lilley et al. | |
| 5,936,613 A | 8/1999 | Jaeger et al. | |
| 5,941,710 A * | 8/1999 | Lampotang et al. | 434/272 |
| 5,954,689 A | 9/1999 | Poulsen | |
| 5,963,196 A | 10/1999 | Nishiumi et al. | |
| 5,986,638 A | 11/1999 | Cheng | |
| 6,017,273 A | 1/2000 | Pelkey | |
| 6,031,222 A | 2/2000 | Carapelli | |
| 6,037,927 A | 3/2000 | Rosenberg | |
| 6,078,311 A | 6/2000 | Pelkey | |
| 6,078,876 A | 6/2000 | Rosenberg et al. | |
| 6,097,499 A | 8/2000 | Casey et al. | |
| 6,097,964 A | 8/2000 | Nuovo et al. | |
| 6,104,379 A | 8/2000 | Petrich et al. | |
| 6,106,299 A * | 8/2000 | Ackermann et al. | 434/81 |
| 6,183,364 B1 | 2/2001 | Trovato | |
| 6,192,432 B1 | 2/2001 | Slivka et al. | |
| 6,241,574 B1 | 6/2001 | Helbing | |
| 6,259,433 B1 | 7/2001 | Meyers | |
| 6,273,728 B1 * | 8/2001 | van Meurs et al. | 434/268 |
| 6,280,327 B1 | 8/2001 | Leifer et al. | |
| 6,293,798 B1 | 9/2001 | Boyle et al. | |
| 6,295,608 B1 | 9/2001 | Parkes et al. | |
| 6,300,038 B1 | 10/2001 | Shimazu et al. | |
| 6,349,301 B1 | 2/2002 | Mitchell et al. | |
| 6,418,329 B1 | 7/2002 | Furuya | |
| 6,470,302 B1 | 10/2002 | Cunningham | |
| 6,546,390 B1 | 4/2003 | Pollack et al. | |
| 6,633,224 B1 | 10/2003 | Hishida et al. | |
| 6,760,751 B1 | 7/2004 | Hachiya et al. | |
| 6,929,481 B1 | 8/2005 | Alexander et al. | |
| 2001/0018354 A1 | 8/2001 | Pigni | |
| 2001/0045978 A1 | 11/2001 | McConnell et al. | |
| 2002/0072674 A1 | 6/2002 | Criton et al. | |
| 2003/0043206 A1 | 3/2003 | Duarte | |
| 2003/0112269 A1 | 6/2003 | Lentz et al. | |
| 2004/0009459 A1* | 1/2004 | Anderson et al. | 434/262 |
| 2004/0076444 A1 | 4/2004 | Badovinac et al. | |
| 2004/0193393 A1 | 9/2004 | Keane | |
| 2005/0123892 A1* | 6/2005 | Cornelius et al. | 434/323 |
| 2005/0187747 A1 | 8/2005 | Paxson et al. | |
| 2005/0289092 A1* | 12/2005 | Sumner et al. | 706/46 |
| 2007/0124128 A1 | 5/2007 | Connacher et al. | |
| 2008/0227073 A1* | 9/2008 | Bardsley et al. | 434/267 |

FOREIGN PATENT DOCUMENTS

| | | |
|---|---|---|
| EP | 0 358 989 B1 | 7/1994 |
| EP | 0 875 819 B1 | 10/2002 |
| GB | 2 237 160 A | 4/1991 |
| GB | 2 347 199 A | 8/2000 |
| WO | WO 96/16397 | 5/1996 |
| WO | WO 96/24398 | 8/1996 |
| WO | WO 96/32679 | 10/1996 |
| WO | WO 00/77689 A1 | 12/2000 |
| WO | WO 01/00630 A1 | 1/2001 |
| WO | WO 01/67297 A1 | 9/2001 |
| WO | WO 03/000319 A1 | 1/2003 |

OTHER PUBLICATIONS

Adelstein, B. et al., Design and Implementation of a Force Reflecting Manipulandum for Manual Control Research, DSC-vol. 42, Advances in Robotics, ASME 1992, pp. 1-12.

Akamatsu et al., Multimodal Mouse: A Mouse-Type Device with Tactile and Force Display, Presence, vol. 3, No. 1 pp. 73-80, 1994.

ATIP98.059: Virtual Reality (VR) Development at SERI (Korea), Asian Technology Information Program (ATIP) Jul. 20, 1998, pp. 1-9.

Aukstakalnis, S. et al., The Art and Science of Virtual Reality Silicon Mirage, 1992, Peachpit Press, Inc., Berkeley, CA, pp. 129-180.

Baigrie, S. et al., Electric Control Loading-A Low Cost, High Performance Alternative, Proceedings, Nov. 6-8, 1990, pp. 247-254.

Bejczy, A., Sensors, Controls, and Man-Machine Interface for Advanced Teleoperation, Science, vol. 208, No. 4450, 1980, pp. 1327-1335.

Bejczy, A. et al., Kinesthetic Coupling Between Operator and Remote Manipulator, International Computer Technology Conference, The American Society of Mechanical Engineers, San Francisco, CA, Aug. 12-15, 1980, pp. 1-9.

Bejczy, A. et al., A Laboratory Breadboard System for Dual-Arm Teleoperation, SOAR '89 Workshop, JSC, Houston, Jul. 25-27, 1989.

Bejczy, A. et al., Universal Computer Control System (UCCS) for Space Telerobots, Jet Propulsion Laboratory, California Institute of Technology, Pasadena, CA, pp. 317-324, 1987.

Bjork, S. et al., An Alternative to Scroll Bars on Small Screens, Play: Applied Research on Art and Technology, Viktoria Institute, Box 620, SE-405 30 Gothenburg, Sweden, pp. 1-2.

Bouguila, L. et al., Effect of Coupling Haptics and Stereopsis on Depth Perception in Virtual Environment, Precision and Intelligence Laboratory, Tokyo Institute of Technology, 4259 Nagatsuta cho Midori ku Yokohama shi 226-8503-Japan, 2000.

Brooks, T. et al., Hand Controllers for Teleoperation: A State-of-the-Art Technology Survey and Evaluation, 1985, NASA Jet Propulsion Laboratory, California Institute of Technology, Pasadena, CA.

Burdea, G. et al., Distributed Virtual Force Feedback, IEEE Workshop on "Force Display in Virtual Environments and its Application to Robotic Teleoperation," May 2, 1993, Atlanta, GA.

Calder, B. et al., Design of a Force-Feedback Touch-Inducing Actuator for Teleoperator Robot Control, Submitted to the Department of Mechanical Engineering and Electrical Engineering in partial Fulfillment of the requirements of the degree of Bachelors of Science in Mechanical Engineering and Bachelor of Science in Electrical Engineering at the Massachusetts Institute of Technology, May 1983.

Caldwell, D. et al., Enhanced Tactile Feedback (Tele-Taction) using a Multi-Functional Sensory System, Dept. of Electronic Eng., University of Salford, Salford, M5 4WT, UK, 1993.

Cyberman Technical Specification, Logitech Cyberman Swift Supplement, Revision 1.0, Apr. 5, 1994, pp. 1-29.

Eberhardt, S. et al., OMAR-A Haptic Display for Speech Perception by Deaf and Deaf-Blind Individuals, IEEE Virtual Reality Annual International Symposium, Sep. 18-22, 1993, Seattle Washington.

Eberhardt, S. et al., Inducing Dynamic Haptic Perception by the Hand: System Description and Some Results, Dynamic Systems and Control, 1994, vol. 1, presented at 1994 International Mechanical Engineering Congress and Exposition, Chicago Illinois, Nov. 6-11, 1994.

Fukumoto, M. et al., Active Click: Tactile Feedback for Touch Panels, NTT DoCoMo Multimedia Labs, Japan.

Gobel, M. et al., Tactile Feedback Applied to Computer Mice, International Journal of Human-Computer Interaction, vol. 7, No. 1, pp. 1-24, 1995.

Gotow, J. et al., Controlled Impedance Test Apparatus for Studying Human Interpretation of Kinesthetic Feedback, The Robotics Institute and Deptartmetn of Mechanical Engineering, Carnegie Mellon University, Pittsburgh, PA 15213, pp. 332-337.

Hansen, W., Enhancing Docuemtns with Embedded Programs: How Ness extends Insets in the Andrew Toolkit, 1990, Information Technology Center, Carnegie Mellon University, Pittsburgh, PA 15213, 1990.

Hasser, C. et al., Tactile Feedback with Adaptive Controller for a Force-Reflecting Haptic Display Part 1: Design, 1996, Armstrong Laboratory, Human Systems Center, Air Force Materiel Command, Wright-Patterson AFB OH 45433.

Hasser, C. et al., Tactile Feedback for a Force-Reflecting Haptic Display, Thesis Submitted to the School of Engineering of the University of Daytona, Dayton OH, Dec. 1995.

(56) References Cited

OTHER PUBLICATIONS

Hasser, C., Force-Reflecting Anthropomorphic Hand Masters, Crew Systems Directorate Biodynamics and Biocommunications Division, Wright-Patterson AFB OH 45433-7901, Jul. 1995, Interim Report for the Period Jun. 1991-Jul. 1995.

Hinckley, K. et al., Haptic Issues for Virtual Manipulation, A Dissertation presented to the Faculty of the School of Engineering and Applied Science at the University of Virginia, in Partial Fulfillment of the Requirement for the Degree Doctor of Philosophy (Computer Science), Dec. 1996.

Howe, R., A Force-Reflecting Teleoperated Hand System for the Study of Tactile Sensing in Precision Manipulation, Proceedings of the 1992 IEEE Conference in Robotics and Automation, Nice, France—May 1992.

Iwata, H., Pen-Based Haptic Virtual Environment, Institute of Engineering Mechanics, University of Tsukuba, Japan, 1993.

Jacobsen, S. et al., High Performance, Dextrous Telerobotic Manipulator with Force Reflection, Intervention/ROV '91, Conference & Exposition, May 21-23, 1991, Hollywood, FL.

Johnson, A., Shape-Memory Alloy Tactical Feedback Actuator, Phase I—Final Report, Air Force SABIR Contract F33-88-C-0541, Armstrong Aerospace Medical Research Laboratory, Human Systems Division, Air Force Systems Command, Wright-Patterson Air Force Base, OH 45433.

Jones, L. et al., A Perceptual Analysis of Stiffness, Experimental Brain Research, 1990, vol. 79, pp. 150-156.

Kaczmarek, K. et al., Tactile Displays, Virtual Environment Technologies, pp. 349-414.

Kelley, A. et al., MagicMouse: Tactile and Kinesthetic Feedback in the Human-Computer Interface using an Electromagnetically Actuated Input/Output Device, Department of Electrical Engineering, University of British Columbia, Canada, Oct. 19, 1993.

Lake, S.L., Cyberman from Logitech, web site at http://www.ibiblio.org/GameBytes/issue21/greviews/cvberman/html, as available via the Internet and printed May 29, 2002.

MacLean, K., Designing with Haptic Feedback, Interval Research Corporation, 1801 Page Mill Road, Palo Alto, CA 94304, 2000.

Mine, M., Isaac: A Virtual Environment Tool for the Interactive Construction of Virtual Worlds, Department of Computer Science, University of North Carolina Chapel Hill, 1995.

Picinbono, G. et al., Extrapolation: A Solution for Force Feedback, Virtual Reality and Prototyping, Jun. 1999, Laval, France.

Wloka, M., Interacting with Virtual Reality, Science and Technology Center for Computer Graphics and Scientific Visualization, Brown University Site, Department of Computer Science, 1995.

eRENA, Pushing Mixed Reality Boundaries, Deliverable 7b.1, Final, Version 1.0.

Real Time Graphics, The Newsletter of Virtual Environment Technologies and Markets, Aug. 1998, vol. 7, No. 2.

1998 IEEE International Conference on Robotics and Automation, May 16-20, 1998, Lueven, Belgium.

\* cited by examiner

SYSTEMS AND METHODS FOR EDITING A MODEL OF A PHYSICAL SYSTEM FOR A SIMULATION

FIELD OF THE INVENTION

The present invention generally relates to simulations and more particularly relates to simulations of medical procedures.

BACKGROUND

Simulations of medical procedures are used in a variety of settings to train medical staff or to allow a surgeon to practice a procedure before performing it on a patient. For example, a simulation may provide graphical images of anatomic and physiologic models representing a patient or part of a patient. The displayed images of the models may then change during the procedure based on the movements and actions of the user. For example, as the user makes incisions and moves surgical tools within the patient, those actions are tracked, within the patient and result in changes to the simulated anatomy and physiology and thus a new image is presented to the user. By providing a responsive, high-quality simulated procedure, a user, such as a surgeon, may be able to practice the surgery in a realistic environment.

However, these simulations are typically extremely expensive and highly-customized by the supplier of the simulation. The computing hardware necessary to provide real-time simulated cause and effect actions as well as perform the calculations needed to accurately model the patient can be significant. Further, a user of the simulation cannot create and import customized patient data or alter existing simulation models, including adding pathologies or adjusting other characteristics, such as age or weight. Additionally, a user of the simulation cannot modify the simulation to incorporate customized messages or content to aid in the use of the simulation, such as training messages or signals.

SUMMARY

Embodiments of the present invention provide systems and methods for simulating medical procedures. For example, in one embodiment of the present invention, a system for simulating a medical procedure comprises a physics module configured to model at least one physical property of a user-defined organic object associated with a patient; a display module configured to cause a display of the user-defined organic object; a script module configured to execute a user-defined medical procedure script; a simulation module in communication with the physics module, the display module, and the script module, the simulation module configured to receive input from a simulated medical apparatus and execute a simulation of the medical procedure based at least in part on the user-defined model of the organic object and the user-defined medical procedure script.

Another embodiment of the present invention comprises a computer-implemented method for simulating a medical procedure comprising the steps of receiving a user-defined organic object associated with a patient, the user-defined organic object comprising at least one physical property; receiving a user-defined medical procedure script; executing a simulation of the medical procedure based at least in part on the user-defined organic object and the user-defined medical procedure script; and outputting an image of the user-defined organic object based at least in part on the simulation. A further embodiment of the present invention comprises a computer-readable medium having program code for executing such a computer-implemented method.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Figure 1:
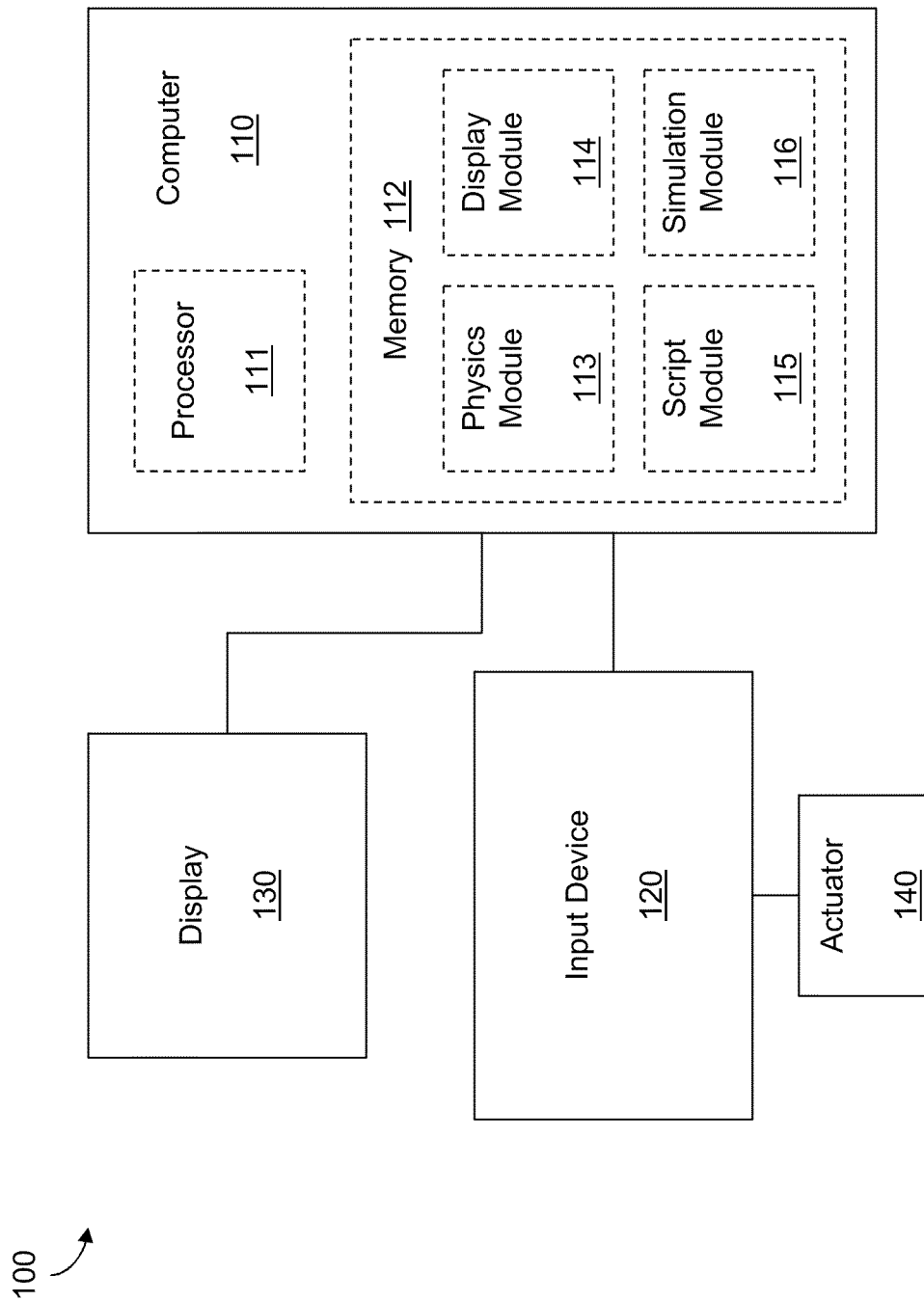
FIG. 1 is a block diagram showing a system for simulating a medical procedure according to one embodiment of the present invention.

Embodiments of the present invention provide systems and methods for simulating a medical procedure.

For example, one embodiment provides a system for editing a medical procedure including a computer running software for editing a medical procedure. In such a system, a user may use the editing system to create and customize a simulation of a medical procedure. For example, the user can select a template describing a patient with some default characteristics. In one embodiment of the present invention, a patient may be a human being. But in other embodiments, a patient may be an animal, such as in an embodiment for use in a veterinary environment, an environment of objects used for skills training exercises, or gaming environment to foster hand/eye coordination with the surgical instruments. The user may then adjust parameters describing the patient, such as the patient's age and general level of health. The user may also adjust more detailed characteristics of the patient, such as the locations and sizes of fatty tissue deposits, adhesions, or pathologies. In addition, the user can select surgical tools to be used with the simulation, and incision and insertion points. Further, the user can edit the simulation of the medical procedure to include scripted events. For example, the user can create and include scripts to provide warning messages to a user of the simulation, such as a medical student, indicating that the student has made an incision in a wrong location. The user may also include information to describe haptic feedback to be output to tools used by a user of the simulation.

Another embodiment provides a system for executing a simulation of medical procedure. In such an embodiment, a user may load a customized simulation created with an editor embodiment of the present invention. The simulation system reads the information in the customized simulation and executes a simulation environment based on the customized simulation information. The simulation system displays a rendered image of a three-dimensional scene from the perspective of the surgeon or a camera inserted into the patient, such as in a laparoscopic surgery. The user manipulates simulated surgical tools to perform the simulated medical procedure. The simulated surgical tools may resemble actual surgical tools the user may encounter during an actual surgery and may provide computer-controlled force feedback to the user to simulate the feel of the surgery using the tools. In addition, the simulation system may detect events during the simulated procedure and execute scripts associated with the events. For example, the system may display a message if a user correctly executes an incision, or display a score based on the user's performance of the simulated procedure. Additionally, user performances may be stored in a database. The user performance data can be aggregated for identifying areas for improvement, identifying progress made, and other purposes.

The foregoing embodiments are intended to provide an introduction to the subject matter of the following detailed disclosure and are not intended to limit the scope of the disclosure in any way. It should be noted that the use of the term 'or' in this specification is intended to include both the inclusive and exclusive meanings and is not intended to indicate a choice restricted to only one alternative.

Illustrative Simulation of a Medical Procedure

Referring now to the figures in which like numbers refer to like elements throughout the several drawings, FIG. 1 is a block diagram showing a system for simulating a medical procedure according to one embodiment of the present invention. According to the illustrative embodiment shown in FIG. 1, a system 100 for simulating a medical procedure comprises a computer 110, an input device 120, a display 130, and an actuator 140 in communication with the input device 120. The computer 110 comprises a processor 111 and a computer-readable medium 112 in which is stored a physics module 113, a display module 114, a script module 115, and a simulation module 116. Each of the modules 113-116 comprises a software program or is part of a software program. Together, the modules create a framework on which a simulation of a medical procedure may be executed. In other embodiments, the various modules may comprise hardware modules, such as field-programmable gate arrays (FPGAs) configured to perform the various functions of the software modules.

In the embodiment shown in FIG. 1, the system 100 receives a definition of a customized simulation of a medical procedure, or "scene." For example, in the embodiment shown in FIG. 1, a user has created a scene representing a human abdomen, including various internal organs, for use in a laparoscopic appendectomy where the abdomen is from a 47 year-old female with appendicitis. When creating the scene, a user specified the amount of fatty tissue and other characteristics of the patient's abdomen to create a particular environment for students in a medical school or training course.

The scene includes models of organic objects that have information about the organs and tissue within the abdomen or covering the abdomen, such as pathologies, and location and size of fatty deposits and adhesions. The models also include physical properties of the different components of the abdomen, such as elasticity characteristics, hardness characteristics, or other characteristics that affect how the abdomen may appear or react to physical interactions. Further, the models include graphical information to allow the abdomen to be displayed to the user. The models are stored in a model file on a computer-readable medium for use with the framework.

The user has also created a script for use in the scene. The script includes information to cause the system 100 to provide helpful graphics to identify possible incision points, areas of interest (including areas to avoid), as well as textual information that may be displayed to the user upon the occurrence of a pre-determined event. For example, if a student makes an incision in the wrong place, a scripted message may be displayed indicating the error. The script also includes programming to allow the system 100 to score the user on his performance, and to display the score to the user after the procedure has been completed. The script is stored in a script file on a computer-readable medium for use with the framework.

To execute a simulation using the system 100, the system 100 loads the information stored in the model file and the script file. In one embodiment, the model file and the script file may comprise a plurality of files. In another embodiment, a single file may comprise model and script information. The system 100 executes the simulation by executing the simulation module 116. The simulation module 116 manages the execution of the simulation by receiving inputs from a user interacting with the simulation, such as from the input device 120, and by transmitting or receiving information from one or more of the modules 113-115.

For example, the simulation module 116 receives an input signal from an input device 120, such as a simulated surgical tool, indicating movement of the input device 120. The simulation module 116 then employs the physics module 113 to calculate interactions between the model of one or more organic objects and the simulated surgical tool to determine a response of the models to the surgical tool. The physics module 113 determines the model's response to the surgical tool and sends information to the simulation engine that indicates a deformation of the model. The simulation module 116 then sends the physics information to the display module 114. The display engine 114 uses the physics information to generate a graphical representation of the model comprising the deformation, and transmits a display signal to the display 130 to cause the display 130 to display the graphical representation. The simulation module 116 may also transmit a signal to the input device 120 configured to cause the actuator 140 to output a haptic effect to the input device 120. The simulation module 116 may also record a user's actions in the simulation to allow replay of the user's performance, or it may store scoring information for the user in a database to allow aggregation of the information for overall scoring or performance tracking.

The simulation module 116 also determines a script signal based on the input signal or information from the physics engine. The script signal is sent to the script module 115, which determines whether a scripted event should occur. If a scripted event has occurred, the script engine executes program code within the script associated with the scripted event to cause the scripted event to occur. For example, if the user has made an incision in the correct location and of the correct size, a portion of a script may be executed to display a message or graphic, such as a green light, to indicate that the user has correctly executed the portion of the procedure.

Each of these modules works in concert to provide an immersive, realistic, customized simulation of a medical procedure.

Figure 2:
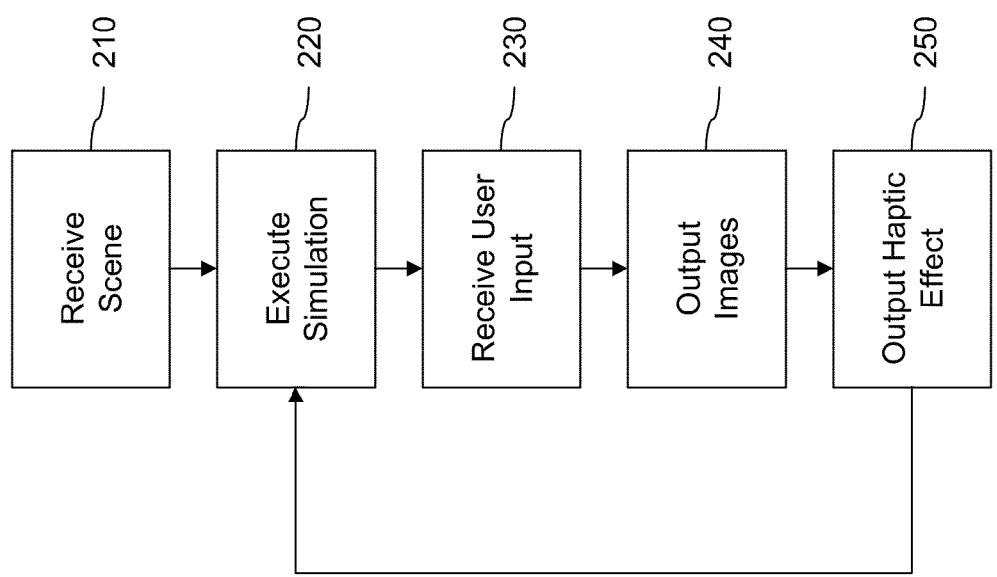
FIG. 2 shows a method for simulating a medical procedure according to one embodiment of the present invention.

Referring now to FIG. 2, FIG. 2 shows a method 200 for simulating a medical procedure according to one embodiment of the present invention. The method 200 will be described with respect to the system shown in FIG. 1. The embodiment shown begins in block 210 with the computer receiving a user-defined scene. For example, the computer 110 may load a user-defined scene from a computer-readable medium, such as a hard drive or CD-ROM. In one embodiment, the computer 110 may receive the user-defined scene from a server that is remote from the computer 110. In some embodiments, a remote server may comprise a web server, an FTP server, or a file server.

In this embodiment, the scene comprises an organic object associated with a patient, a description of a surgical tool, and a user-defined medical script. In some embodiments of the present invention, a scene may be user-defined based on a user's selection of components for the scene, though the components may not have been modified by the user. In some embodiments of the present invention, a scene may be user-defined based on both a user's selection of components for the scene as well as a user's modification of the components selected for the scene. Systems and methods for generating a user-defined scene are described in more detail with respect to systems and methods for editing a medical procedure simulation in other parts of this specification.

One example of a user-defined scene may comprise information describing a patient's abdomen, including the location and physical characteristics of the patient's abdominal muscles, intestines, stomach, liver, and pancreas. The physical characteristics may comprise user-defined characteristics including adhesions, fatty deposits, and pathologies, such as growths, tumors, or defects. For example, one organic object may comprise a patient's liver that includes a benign tumor.

In addition to the organic object, the scene in this embodiment also comprises a description of a surgical tool. In one embodiment, a description of a surgical tool may be received from a data file having parameters describing the type of tool as well as characteristics of the tool, such as its size and shape. In another embodiment, a description of a surgical tool may be received from a server remote from the computer 110.

The user-defined scene further comprises a user-defined script. A script may comprise program code and be employed in a simulation to provide information to a user or to affect the execution of the simulation. For example, one user-defined script may comprise program code to determine if a user's actions are an error and display a message indicating the error or to output a sound indicating the error. Or, the script may be configured to cause a haptic effect to be output to indicate a response to a user's actions. For example, if a user moves simulated surgical tool near an area where the tool should not be used, the script may cause a slight vibrational effect to be output to the simulation input device 120. The script may increase the intensity of the vibration if the user moves the tool closer to the prohibited area, and may apply a braking force to indicate the direction of motion is incorrect.

After receiving the user-defined scene, the method 200 proceeds to step 220 and executes the simulation based on the user-defined scene. For example, in one embodiment of the present invention, the simulation is executed by a simulation module 116. As part of the execution, input signals from the simulation input device 120 are received by the simulation module 116. The simulation module 116 transmits messages to the physics module 115 to determine collisions between objects in the scene, such as between the simulation surgical device and an organic object, and determine deformations of objects in the scene. The simulation module 116 also transmits messages to the display module 114 to provide a view of the scene from a viewpoint, such as a camera's viewpoint or the user's viewpoint. The simulation module 116 also transmits messages to the script module 115 to identify events and to execute the appropriate script.

While executing the simulation, the system may proceed to step 230 and receive user inputs. For example, in one embodiment, the computer 110 may receive user inputs, such as input signals indicating a movement of a simulation input device 120. For example, the computer 110 may receive signals from sensors within the simulation input device 120 indicating a movement of the device 120. The computer 110 may process the sensor signals to determine a position and orientation of the input device and a corresponding position and orientation of the simulation surgical device. In one embodiment, the computer 110 may receive a signal indicating that an additional tool may be employed. For example, if a user inserts a simulated cannula into an incision, the user may later insert a catheter or other tool into the cannula. Thus, a user may indicate to the simulator that a catheter tool should be activated to be inserted into the cannula Further, while executing the simulation, the system may proceed to step 240 and output images to a display 130 corresponding to a view of the scene. For example, in one embodiment of the present invention, the system may receive information from a sensor worn by a user indicating a location and orientation of the user's head. This sensor information may be used to determine a viewpoint from which an image should be generated based on the organic objects in the scene. In one embodiment, in addition to such a sensor indicating the location and orientation of the user's head, a simulation surgical device may be defined to comprise a simulated camera to allow the user to view the interior of the patient. In such an embodiment, a viewpoint may be determined based on the position and orientation of a simulation input device 120 corresponding to the simulation surgical device having the camera.

To generate and output the images, a display module 114 may be employed. The simulation module may transmit a message comprising a viewpoint to the display module 114. The display module 114 may then generate an image based on the organic objects in the scene and the viewpoint. In one embodiment, the simulation module may transmit a message comprising a plurality of viewpoints to the display module 114. For example, in such an embodiment, an image may be generated comprising views from both of the location and orientation of the user's head and a simulated camera. In one embodiment, multiple images may be generated in succession to create a real-time view of the scene based on user inputs.

While executing the simulation, the method may proceed to step 250 and output a haptic effect. For example, in one embodiment of the present invention, the simulation module 116 may transmit a message to the script module 115. In response, the script module 115 may execute a script that may determine a haptic effect is to be output. In such an embodiment, the script module 115 may transmit a message to the simulation module 116 to generate a signal to cause a haptic effect to be output to an input device 120. For example, the script module 115 may determine that a vibration should be output. The script module 115 generates and transmits a message to the simulation module 116 comprising a description of the haptic effect. In one embodiment, the description may comprise a high-level haptic command indicating a vibration having a frequency, amplitude, and duration. In such an embodiment the simulation module 116 may generate an actuator signal configured to cause the actuator to output the haptic effect. In another embodiment, the simulation module 116 may transmit the high-level haptic command to the input device 120, which may then generate an actuator signal configured to cause the actuator to output the haptic effect. In another embodiment, the script message may generate a low-level haptic command comprising information to directly command the actuator, which may be transmitted by the simulation module 116 to the input device 120 or the actuator. In some embodiments, the script module 115 may transmit the haptic command to the input device 120 or the actuator rather than sending a message to the simulation module.

In some embodiments, the simulation module 116 may determine a haptic effect should be output. For example, a manipulation of the input device may indicate the movement of the simulation surgical device into tissue. The simulation module may determine that a braking force is to be output to simulate resistance to movement of the input device 120. Still further embodiments may determine and generate default haptic effects, such as the application of a braking force to indicate the completion of a simulation or an active force to simulate a beating heart.

Illustrative Editor of a Simulation of a Medical Procedure

Figure 3:
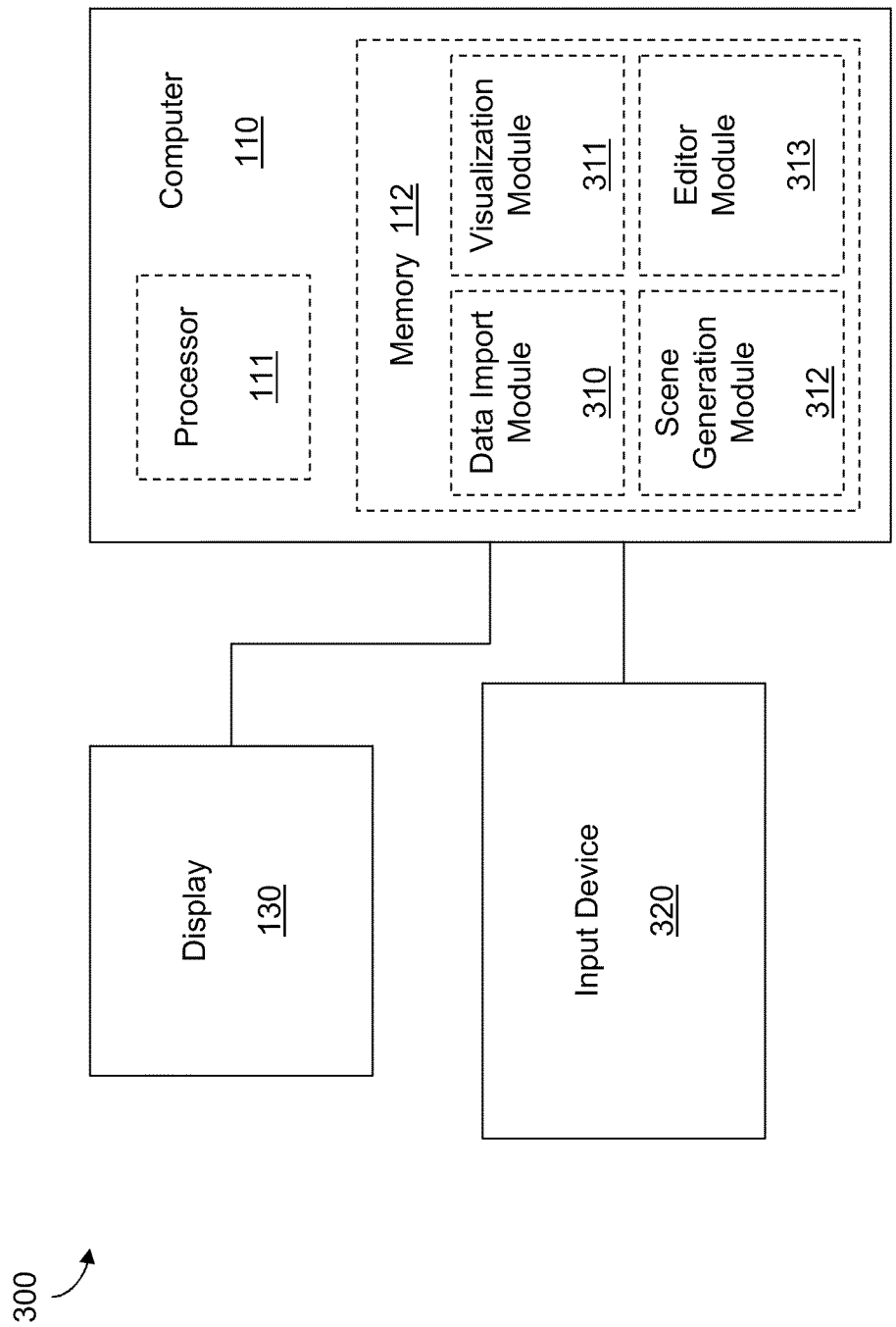
FIG. 3 is a block diagram showing a system for editing a medical procedure simulation according to one embodiment of the present invention.

Referring now to FIG. 3, FIG. 3 is a block diagram showing a system 300 for editing a medical procedure simulation according to one embodiment of the present invention. According to the illustrative embodiment shown in FIG. 3, a system 300 for editing a medical procedure comprises a computer 110, an input device 320, and a display 130, though other input devices, such as touch-sensitive devices, may be used. The computer 110 comprises a processor 111 and a computer-readable medium 112 in which are stored a data import module 310, a visualization module 311, a scene generation module 312, and an editor module 313.

The editor module (or "editor") 313 comprises program code for allowing a user to edit a simulation of a medical procedure. It provides a graphical user interface (GUI) to allow a user to interact with the editor 313, and provides options for adding, customizing, or removing components of a simulation. In the embodiment shown in FIG. 3, the editor 313 also provides a text editor, which allows a user to enter program code for one or more scripts that can be included within a simulation. The GUI, in this embodiment, further comprises a window configured to show a graphical representation of the configuration of the medical simulation based on the user's inputs. For example, the editor can display a representation of a patient, a representation of one or more surgical tools, and representations of different views of a surgical procedure, such as views of different locations within the patient at different points along a timeline for a surgery.

The GUI also provides tools to allow a user to define and manipulate components of a simulation, such as internal organs, incision points, and tissue and adhesion characteristics. Thus, by interacting with the various GUI elements and by manipulating an input device, such as a mouse or a keyboard, a user may create and edit a customized simulation of a medical procedure.

In the embodiment shown, the editor 313 also comprises the portion of the system 300 that coordinates the display of information to the user to allow the user to create and customize a simulation. The remaining components of the system 300 are employed by the editor 313 to provide different functionality to the user.

The system 300 further comprises a visualization module 311 that provides graphical rendering of physical models to be displayed in the editor 313. The visualization module 311 comprises a rendering engine configured to receive information relating to one or more physical models to be displayed and generates a graphical representation based at least in part on the one or more physical models. The rendering engine may also receive information relating to a location and orientation of a viewpoint of a user of the editor to provide an accurate representation of the physical models from the viewpoint.

The data import module 310 may be used by the editor 313 to import data into a simulation. For example, a user may wish to load a previously customized model of an internal organ, or a new simulated surgical tool. The editor 313 will invoke the data import module 310 to load the requested information and provide it to the editor 313 in a format usable by the editor 313.

The scene generation module 312 provides functionality for accepting data describing a scene, such as model information (including physical and material properties), patient information, surgical tool information, and script information, and synthesizing the parameters into one or more simulation files that may be stored on a hard disk or other computer-readable medium. The simulation files may then be loaded by a simulator to provide an interactive simulation of the scene.

Figure 4:
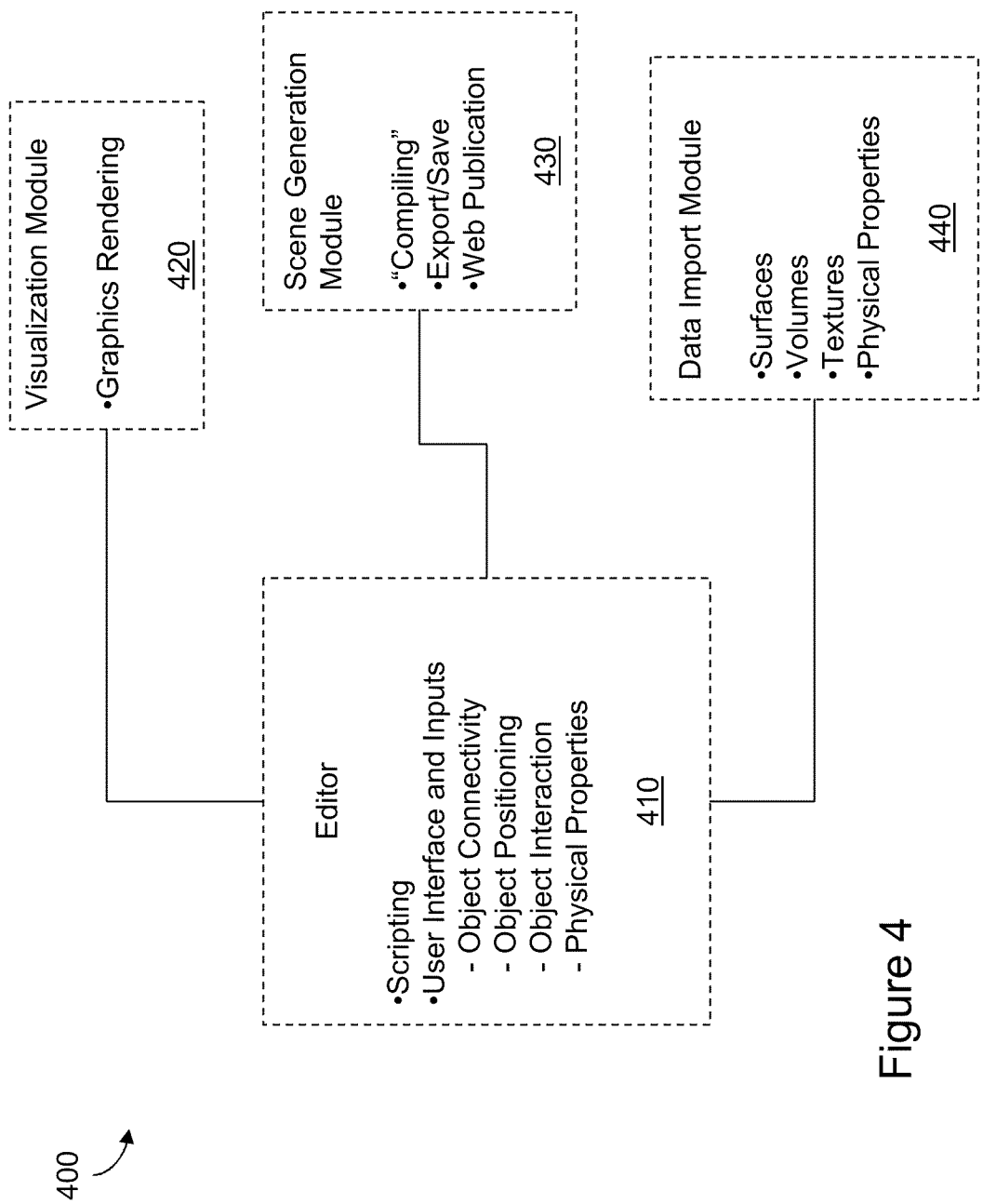
FIG. 4 is a block diagram showing a system for editing a medical procedure simulation according to one embodiment of the present invention.

Referring now to FIG. 4, FIG. 4 is a block diagram showing a system 300 for editing a medical procedure simulation according to one embodiment of the present invention. The system 400 shown in FIG. 4 will be described with respect to computer and hardware components of the system 300 shown in FIG. 3. The system 400 shown in FIG. 4 comprises an editor 410, a visualization module 420, a scene generation module 430, and a data import module 440.

In the embodiment shown in FIG. 4, the editor module (or "editor") 410 comprises the interface to a user for creating and editing a simulation of a medical procedure. It provides a GUI to the user, processes inputs from the user, and maintains simulation configuration parameters that may be customized by the user. It also handles sending requests to the other modules when needed, such as when a user requests to import a customized model of an organic object (e.g. a custom model of a heart) to be embedded within a simulation, when rendering views of the simulation, or when packaging the simulation to be stored on a computer-readable medium in a format usable by a simulation system, such as the one shown in FIG. 1.

In the embodiment shown in FIG. 4, the editor module 410 is configured to execute on the processor 111 and to manage the system 400 to allow a user to create a user-defined medical procedure simulation, also referred to as a "scene." After the editor module 410 has been started, a user interacts with the system 400 by manipulating the input device 320, which may comprise a mouse and a keyboard. The editor module 410 generates a GUI to be displayed on the display 130 and receives input signals from the input device 320, which allows the user to interact with the editor to define and edit a simulation.

The editor module 410 allows a user to define the type of medical procedure to be created. For example, the editor module 410 may allow a user to select a particular procedure or a location of a patient's body, identify the organs and tissue included within simulation, and specify other characteristics of the patient, such as an age or overall level of health. By specifying characteristics of a patient, the part of the patient to be the focus of the procedure, and characteristics of organs and tissues to be included in the simulation, the user can define a scene.

In addition to allowing the user to specify various aspects of a scene, the editor 410 also provides a graphical representation of the scene, or part of the scene, to the user by transmitting a signal to the visualization module 420. The visualization module 420 generates a visualization signal configured to cause a display of a view of an organic object. For example, the visualization module 420 is configured to generate a three-dimensional visual representation of one or more of a patient's internal organs. In the embodiment, the patient is 47 years-old and has a benign growth on the interior wall of her large intestine. The editor 410 transmits a signal to the visualization module 420, the visualization signal comprising the patient's age and parameters describing the benign growth. The visualization module then generates a visualization signal configured to cause the display of a view of the patient's large intestine with characteristics associated with a 47 year-old female patient and comprising the benign growth, based at least in part on the signal received from the editor 410.

In addition, the visualization module 420 can generate a three-dimensional interior view of a patient. For example, an interior view of a patient may simulate a view a surgeon may see on a video monitor during a laparoscopic surgery, thus allowing a user of the editor to adjust visual settings or placement of adhesions or fat deposits to accurately replicate a true surgery, or a condition in particular patient that the user had encountered. Alternatively, a three-dimensional view may allow a user to view the scene from any viewpoint to fully view and customize the scene.

To generate a visualization signal, the visualization module 420 analyzes scene information, including characteristics of the patient, models of physical objects within the scene (e.g. organs and tissue), and a user-selected viewpoint. The visualization module 420 generates a graphical representation of the scene using a rendering engine and transmits a visualization signal comprising the graphical representation to be displayed. In one embodiment, the visualization signal is transmitted to a graphics adapter within the computer 110 to be output on the display 130 or may be transmitted to another computer, such as over a network or the Internet as described below with respect to FIG. 5. In another embodiment, the graphical representation is transmitted to the editor module 410, which transmits the graphical representation to a file to be stored on a computer readable medium. For example, in the embodiment shown, the customized simulation comprises several internal organs that are represented by three-dimensional wire meshes comprising vertex and edge information. The rendering engine uses the vertex and edge information to calculate the appearance of each model from a viewpoint. In another embodiment, volumetric elements, such as Voxels, to represent objects within the scene.

The visualization module 420 may also receive information describing the location of fat deposits added by a user of the system 400. In one embodiment of the present invention, the visualization module may generate a three-dimensional wire mesh representing the fat deposits. For example, in one embodiment of the present invention, the user may specify the location of a fat deposit. The user may also specify a volume defining the size and shape of the fat deposit, such as by layering fat deposits to create increased thickness of the deposit. The visualization module 420 may then use points on the surface of the user-defined volume as vertices and may generate a three-dimensional triangular mesh based at least in part on the vertices.

Using the various three-dimensional wire meshes, the visualization engine employs a rendering engine to create a graphical representation of all of the meshes. The rendering engine displays textures, bump maps, and coloring information applied to meshes to create a realistic three-dimensional graphical representation of the scene from the selected viewpoint. The graphical representation is then embedded in a visualization signal, which is transmitted to cause the display of the graphical representation. In one embodiment of the present invention, the system 300 then displays the graphical representation on the display 130. Such a display helps provides a realistic and accurate simulation of a medical procedure to a user of the system.

In addition to allowing a user to fully-customize a new scene, the system 300 is capable of importing data from an existing scene, customized models of physical objects, scripts, simulated surgical tools, and other information that may be incorporated into a scene. In the embodiment shown in FIG. 3, the data import module 340 is configured to receive information describing at least one of a simulation of a medical procedure, a model of an organic object, a model of a surgical tool, or a script. For example, a user may have created a specialized model of a human heart using an embodiment of the present invention, or with another editor capable of creating a model of a physical object, and stored the specialized model within a data file stored on a computer-readable medium. The system 300 uses the data import module 340 to access the information stored within the data file and allow the information to be embedded within a customized simulation. For example, the specialized model of the heart may be incorporated into a customized simulation of a heart surgery. The data import module 340 is configured to be able to accept a wide variety of file formats in which a model of a physical object may be stored, such as in a model file from an editing tool such as Maya or 3D Studio Max.

In addition to importing models of organic objects, the data import module 340 is configured to import existing simulations of medical procedures or scripts, such as simulations created by other users that may be further customized or scripts that may be incorporated into a customized simulation. Additionally, the data import module 340 can import models of surgical tools. For example, one embodiment of the present invention may comprise a default set of tools. However, a user may wish to use a tool that is not one of the default tools. The user may obtain a model of the desired surgical tool and employ the system 300 to import the model of the surgical tool into a customized simulation. Suitable tools, such as grasper tools, scissor tools, and needle driver tools may be imported according to some embodiments.

While creating a scene, a user may create a simulation script that may be employed as part of the scene by the simulation framework during execution. In the embodiment shown in FIG. 4, the editor module 410 comprises a script editor for creating and editing scripts. A script may include information to cause the system 100 to execute the simulation in a particular way or to provide prompts or other information on the screen for the user. For example, the script may specify that the first time the simulation is executed, the user will have the option to observe a pre-defined execution of the procedure, similar to watching a video of the procedure, but shown within the simulation environment using the customized models. Alternatively, the script may cause a system for simulating a medical procedure, such as the system 100 shown in FIG. 1, to display relevant information to the user during the simulation, such as graphical cues indicating incision points, warning messages, positive feedback, a score indicating the quality of the user's performance, or other information that may be useful to a simulation user or instructor. After the user has created the script, it may be stored in a computer-readable medium using a file format recognized by the framework, or it may be incorporated into the scene by the editor 410 or the scene generation module 330.

The system 400 also includes a scene generation module 330 for generating a self-contained customized simulation scene that may be saved to a computer-readable medium as a file or group of files. The file or files may then be employed by a system for simulating a medical procedure, such as the system 100 shown in FIG. 1. For example, a user may create a scene of an appendectomy on a 27 year-old healthy, slightly over-weight woman. The scene comprises a plurality of models of organic objects, several scripts related to scoring a medical student on various aspects of the procedure, and two surgical tools. The scene further comprises a plurality of user-defined fat deposits and adhesions, as well as user-defined lighting conditions and trocar locations.

In the embodiment shown in FIG. 4, the scene generation module 430 is configured to receive information from the editor module 410 that describes the scene. In this embodiment, the editor module 410 transmits a signal to the scene generation module 430 comprising information about the scene, including information describing the models of organic objects, the scripts, the simulated surgical tools, and other user-customized characteristics, including characteristics of the patient and a pathology. In some embodiments, the editor module 410 may provide a pointer to data stored in memory to the scene generation module 430, while in other embodiments, the editor module 410 may transmit the information to the scene generation module 430. For example, in one embodiment, a scene generation module 430 may execute on a computer remote from the user's computer, such as on a web server. In such an embodiment, customizations stored in memory on the user's computer may be transmitted to the web server to generate the scene.

In one embodiment, the scene generation module 430 generates a scene by aggregating all of the information describing the simulation into in one or more data files usable by a system for simulating a medical procedure, such as the embodiment shown in FIG. 1. For example, in one embodiment of the present invention, the scene generation module 430 generates a plurality of files for the scene. According to the embodiment, a first file comprises information describing the models of organic objects used in the scene, including pathologies present in the organic objects as well as customizations of the organic objects based on characteristics of the patient. A second file comprises the scripts used by the scene. A third file comprises the simulated surgical tools used in the simulation. A fourth file comprises information describing fat deposits and adhesions, such as sizes, shapes, locations, and other parameters. In another embodiment, the information describing the simulation is stored in a single file. Further embodiments may use different partitioning of data into different non-volatile computer-readable storage media.

Structurally, in the embodiment shown in FIG. 4, the system 400 comprises distinct software components that are connected via application programming interfaces (APIs). The modules are programmatically distinct components of a single software program. For example, the visualization module 420 comprises a discrete set of program code that communicates with the editor 410 via an API that may be used within the program code for the editor. Similarly, the scene generation module 330 is configured to receive information from the editor 410 through an API. For example, in one embodiment, these distinct modules may be embodied within DLLs. However, other embodiments may provide alternate architectures.

Figure 5:
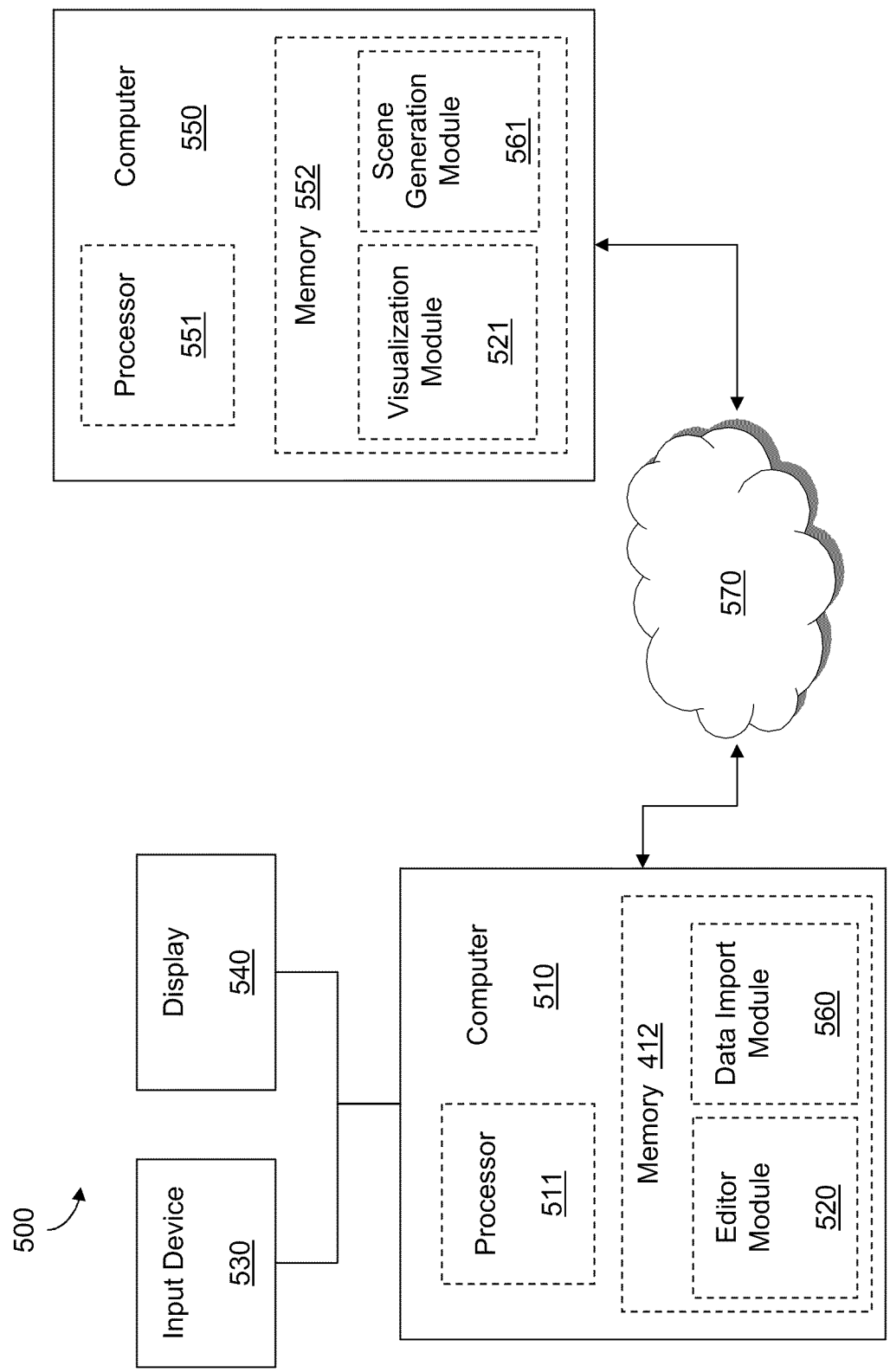
FIG. 5 is a block diagram showing a system for editing a medical procedure simulation according to one embodiment of the present invention.

Referring now to FIG. 5, FIG. 5 is a block diagram showing a system 400 for editing a medical procedure simulation according to one embodiment of the present invention. The editor module (or "editor") 520 may be provided in a web page that executes program code on a user's computer. But other components of the system 400 may be executed by a web server at another location, i.e., remotely. For example, the user's web browser may provide the editor 520 with a GUI for interacting with the system, and may also provide a visualization engine. But a web server may provide scene generation and file management functionality. Such an embodiment may be useful in a medical school setting where a professor may create simulations while working in his office or at home. Alternatively, a third party may license access to an embodiment of the present invention through a website. Such an embodiment may allow a user to create simulations in a cost-effective manner without needing to purchase the full software application. In another embodiment, users may upload completed simulations to a third-party site for distribution, either as a free download or for purchase.

The system 500 may then provide integrated access to a library of medical simulations that have been developed for use within different classes offered. Thus, the professor can create the simulation remotely, but because the file management and scene generation functionality are handled by the medical school's server, the system 500 may allow immediate access to the completed simulation to students or other staff at the medical school.

Some embodiments of the present invention may provide a way for a user to customize a medical procedure simulation by using a plurality of templates, which in turn may be customized. For example, to allow a user to quickly develop a basic patient model, one embodiment of the present invention allows the user to select basic characteristics of the patient's anatomy from one or more pre-defined templates. This may aid the user in creating a generic patient model quickly, and allow the user to spend more time customizing the specific pathology or condition that will be the focus of the simulation. For example, a procedure such as an appendectomy may be selected that requires little modification by the user. However, some embodiments of the present invention may not employ templates, but instead may allow a user to build a medical procedure simulation from the ground up with few or no pre-defined characteristics. For example, a user may customize a model of a patient with a liver damaged by the patient's alcoholism. In such an embodiment, a user may modify, for example, a hardness of the liver, a size and shape of the liver, and a color of the liver.

Some embodiments of the present invention may provide for the online retrieval of models, scripts, scenes, or other data that may be imported into a scene. For example, a user may create a scene and, using an embodiment of the present invention, access a third party's server to retrieve a model of a new surgical tool. The embodiment may allow the user to provide payment information to purchase a copy of the surgical tool model and then import the model into the scene. Still further embodiments may allow the user to access a virtual "store" that can be browsed for desired models or scenes.

Figure 6:
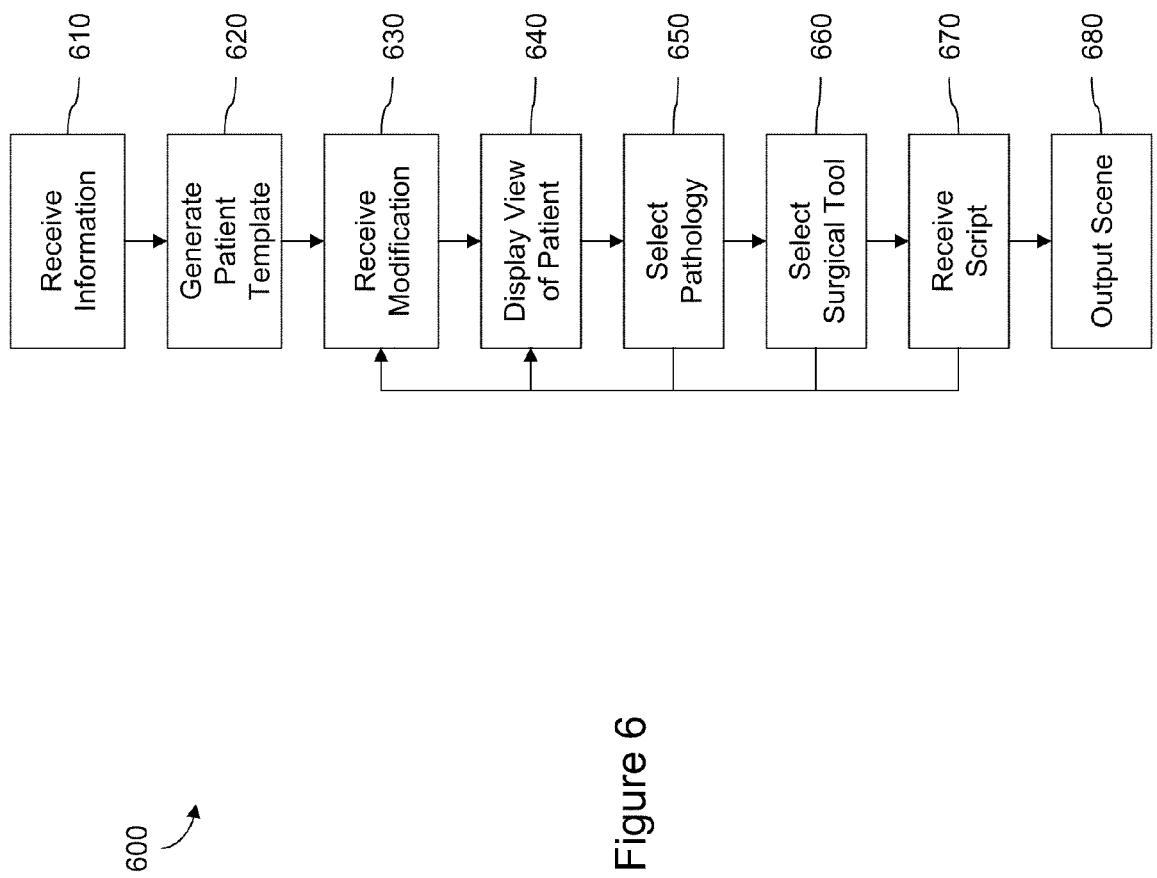
FIG. 6 shows a method for editing a medical procedure simulation according to one embodiment of the present invention.

Referring now to FIG. 6, FIG. 6 shows a method 600 for editing a medical procedure simulation according to one embodiment of the present invention. FIG. 6 will be described with respect to the systems 300, 400 shown in FIGS. 3 and 4. The method 600 begins in step 610 when the system 300 receives information describing at least one of a scene, a model of an organic object, a model of a surgical tool, or a script. For example, in one embodiment, a user may execute computer software on a computer 110 that may read the information from a computer-readable medium. In one embodiment, the computer 110 may receive the information from a web server remote from the computer 110. After receiving the information, the method 600 proceeds to step 620.

In step 620, the system 300 may generate a template of a patient using the information. For example, and as will be described in greater detail below, the system 300 may receive information describing a patient's abdomen, such as a model of the patient's liver. The system may then generate a template such as may be seen in FIG. 7 comprising the information. The user may then edit the template to create a user-defined scene based on the information and the user's inputs.

After generating the patient template, the method 600 proceeds to step 630 where the system 300 receives a modification of a characteristic of the patient template. For example, as may be seen in FIG. 7, a user may select a sex for the patient 710. In the embodiment shown in FIG. 11, a user may select an age 1110 and general level of health 1111 of a patient 710. Still further characteristics may be modified by the user. To receive a modification, the system 300 may receive an input signal from an input device 320. The system 300 may determine that the user has changed parameter based at least in part on the input signal, such as by selecting a radio button, a check box, a drop-down menu item, resizing or moving an organic object, or by entering a value into a text field.

After receiving the modification of a characteristic of the patient template, the system 300 may generate and display a view of the patient to provide feedback to the user modifying the characteristic of the patient template. For example, as may be seen in FIG. 7-23, the system 300 has generated views of the patient based on a user's modification of characteristics of the patient. In one embodiment, the view of the patient may be a two-dimensional view of the patient, such as may be seen in FIGS. 7-18. In one embodiment, the system 300 may generate a three-dimensional view of the patient, such as may be seen in FIGS. 19-23. A further embodiment may be capable generating both a two-dimension and a three-dimensional view of the patient. In one embodiment, the view is generated by the visualization module 311, 420 of the system 300, 400. In one embodiment, a view may be loaded from a computer-readable medium and displayed on the display 130. In another embodiment, a view may be received from a server remote from the system 300 and displayed on the display 130. After generating and displaying the view of the patient, the method 600 may return to step 630 to receive further modifications. Or the method 600 may proceed to step 650.

In step 650, a user may select a pathology associated with the patient. For example, a user may select a growth associated with an organic object associated with the patient. In one embodiment, a user may select a defect associated with an organic object associated with the patient. For example, in the embodiment shown in FIG. 13, a user may select a pathology 1320 from a list of pathologies. In another embodiment, a user may define a new pathology or may import a pathology. After receiving a selection of the pathology, the method 600 may return to step 640 to update the view of the patient, or step 630 to receive further modifications of characteristics of a patient. Or the method 600 may proceed to step 660.

Figure 15:
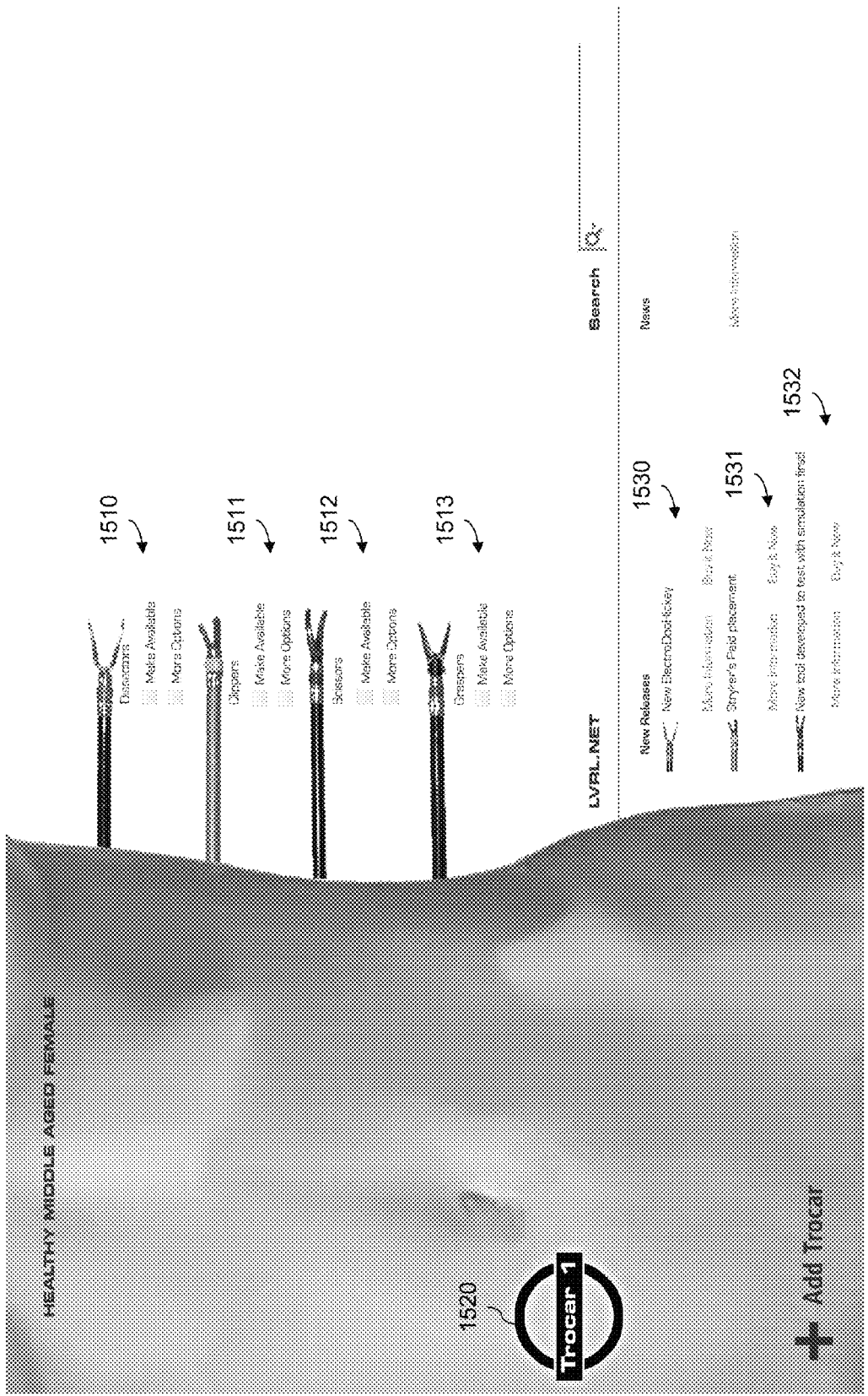
Figure 16:
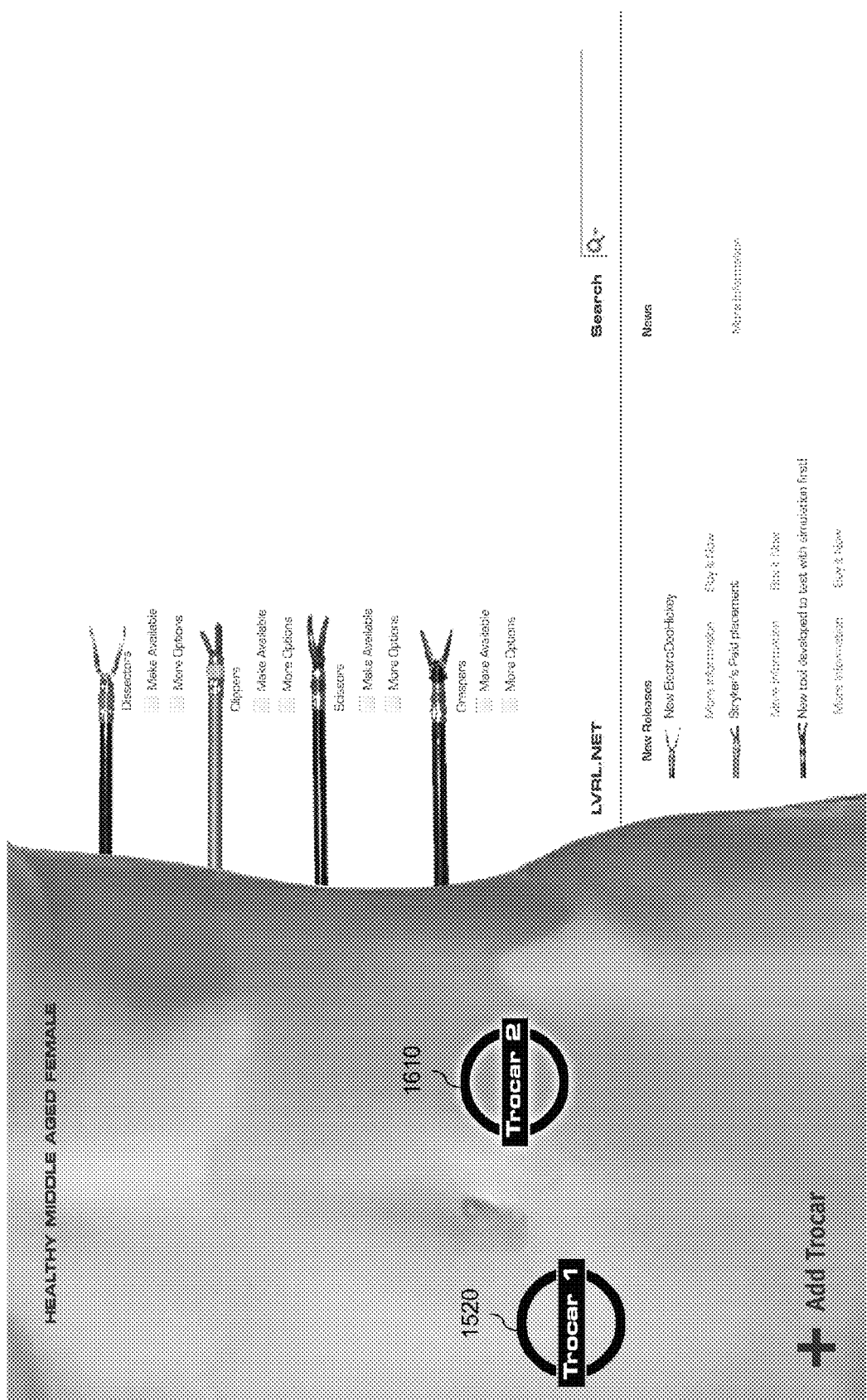

In step 660, a user may select one or more surgical tools to be included in the user-defined scene. For example, in one embodiment, a user may select a tool from a selection of tools provided by the system 300. FIG. 15 shows one embodiment in which a user may select a tool provided by the system 300. In another embodiment, a user may select a tool available from a server remote from the system 300. The embodiment shown in FIG. 15 also shows tools available from a web server. In such an embodiment, the system 300 may employ a data import module 310 to receive and import information describing the selected tool into the user-defined scene. After receiving a selection of a surgical tool, the method 600 may return to step 630 to receive further modifications of characteristics of the patient, or it may return to step 640 to update a view of the patient. Alternatively, the method 600 may proceed to step 670.

In step 670, the system 300 receives a script. For example, in one embodiment, a user may employ the system 300 to write program code to be incorporated into a script, such as by using a text editor component of the system. In such an embodiment, the system 300 may provide text editing capabilities. In one embodiment, the system may comprise information associated with pre-defined events that a user may select. For example, the system may comprise script program code to determine the occurrence of an event and to output messages or haptic effects associated with the occurrence of the event. In another embodiment, a user may generate a script using another software program and may import the script into the scene. In such an embodiment, the system 300 may employ a data import module 310 to import the script. After receiving the script, the method may return to step 630 to allow the user to make additional modifications to the user-defined scene, or to step 640 to display a view of the patient. Alternatively, the method may proceed to step 680.

In step 680, the system 300 generates a user-defined scene based at least in part on the received information in step 610, the patient template, the surgical tool, and the pathology. The system 300 generates the user-defined scene and stores it to a computer-readable medium. For example, in one embodiment the system may generate one or more files, or a package of files, comprising the user-defined scene. In such an embodiment, a user may transfer the files to a portable computer readable medium, such as a compact disc, or upload the files to a server to be made available to other users of systems and methods for editing or simulating a medical procedure.

The foregoing methods describe some embodiments of the present invention, but are not intended to be limiting. Further the steps described with respect to the foregoing embodiments are not required to be performed in the order in which they were described. Steps may be performed in different orders, additional steps may be performed, and in some embodiments, one or more steps may be omitted.

FIGS. 7-23 show screenshots of an editor for editing a medical procedure simulation according to one embodiment of the present invention and will be described in relation to the system 300 shown in FIG. 3 and the method 600 shown in FIG. 6. In the embodiment shown in FIGS. 7-23, a user is constructing a simulation of a surgery relating to the patient's small intestines.

Figure 7:
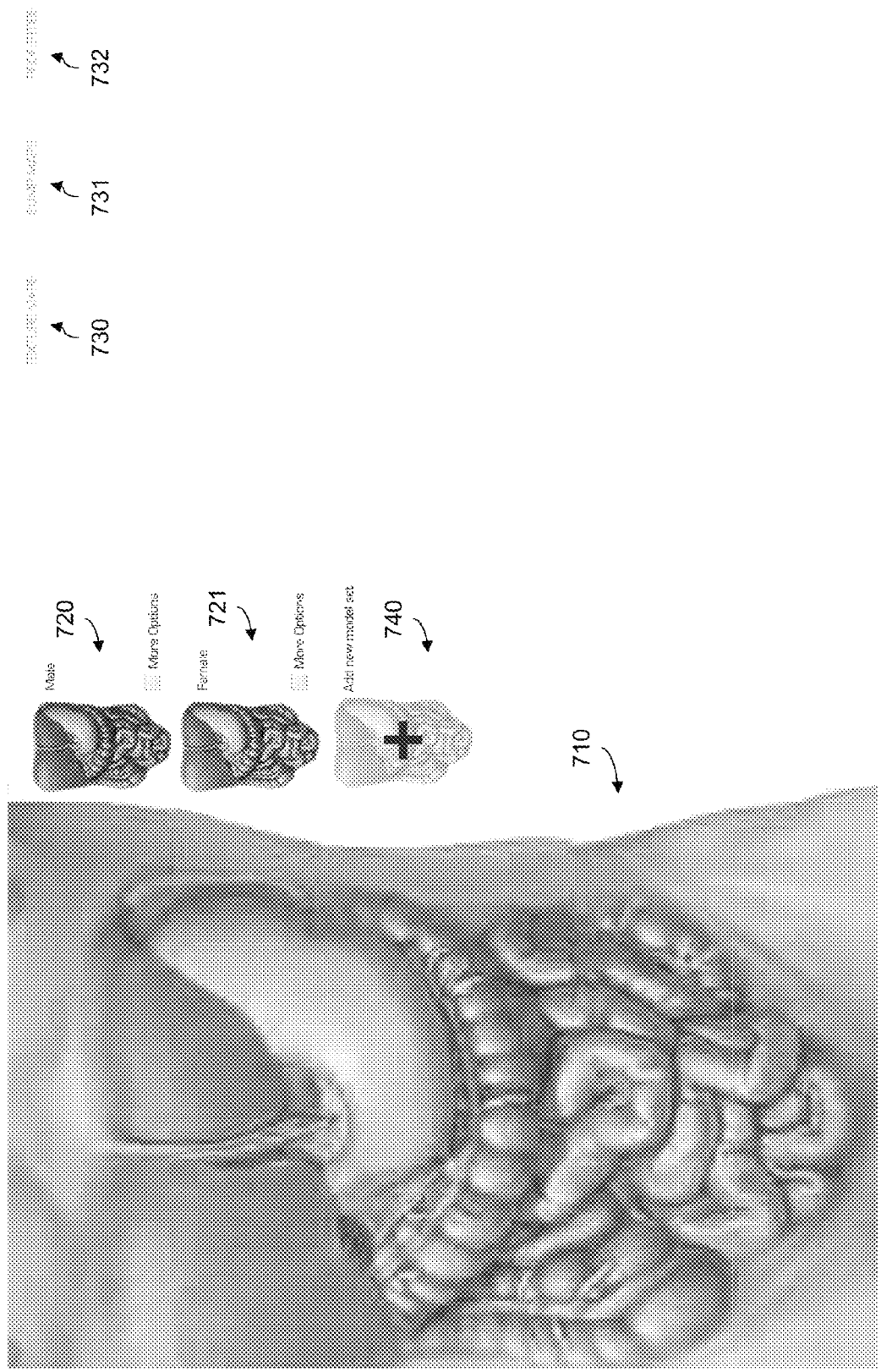
FIGS. 7-23 are screenshots of an editor for editing a medical procedure simulation according to one embodiment of the present invention.

In FIG. 7, the system 300 provides a template for configuring a medical procedure simulation. In the embodiment shown in FIG. 7, the user is presented with a torso view 510 of a hypothetical patient. To provide this view to the user, the editor 213 has generated a graphical user interface view comprising a menu 720 with options 721, 722 for specifying the sex of the patient and output the view to a display. Further, the editor has additional menu options that are not available for selection by a user: Texture Maps 730, Bump Maps 731, and Properties 732. The editor indicates that the menu options are not available by displaying them in a faded, gray color. However, such menu options may allow a user to select texture information associated with a model, such as texture information indicating a healthy intestine, a liver with cirrhosis, or an infected kidney.

A further option is provided to the user: the system 300 allows the user to add a new model set 540 to the simulation. The functionality with regards to this option will be described in greater detail below, but this option can allow a user to import a previously defined patient template that may be used as the basis for a new simulation.

In the embodiment shown in FIG. 5, the system 300 has requested the visualization module to display a generic torso view 710 of a patient, and the visualization module has loaded a model and rendered a model for the system 300. The rendered model is displayed for the user within the GUI. In the embodiment shown in FIG. 5, the model is a two-dimensional depiction of a patient's torso 710 and requires very little rendering prior to display. For example, in this embodiment, the torso 710 is loaded from a two-dimensional JPEG image file. In some embodiments, the visualization module may not render two-dimensional images, but may only be employed for three-dimensional rendering. In other embodiments, both types of images may be displayed.

After a user has selected the sex of the patient, a new view is shown to the user which reflects the choices made.

Figure 8:
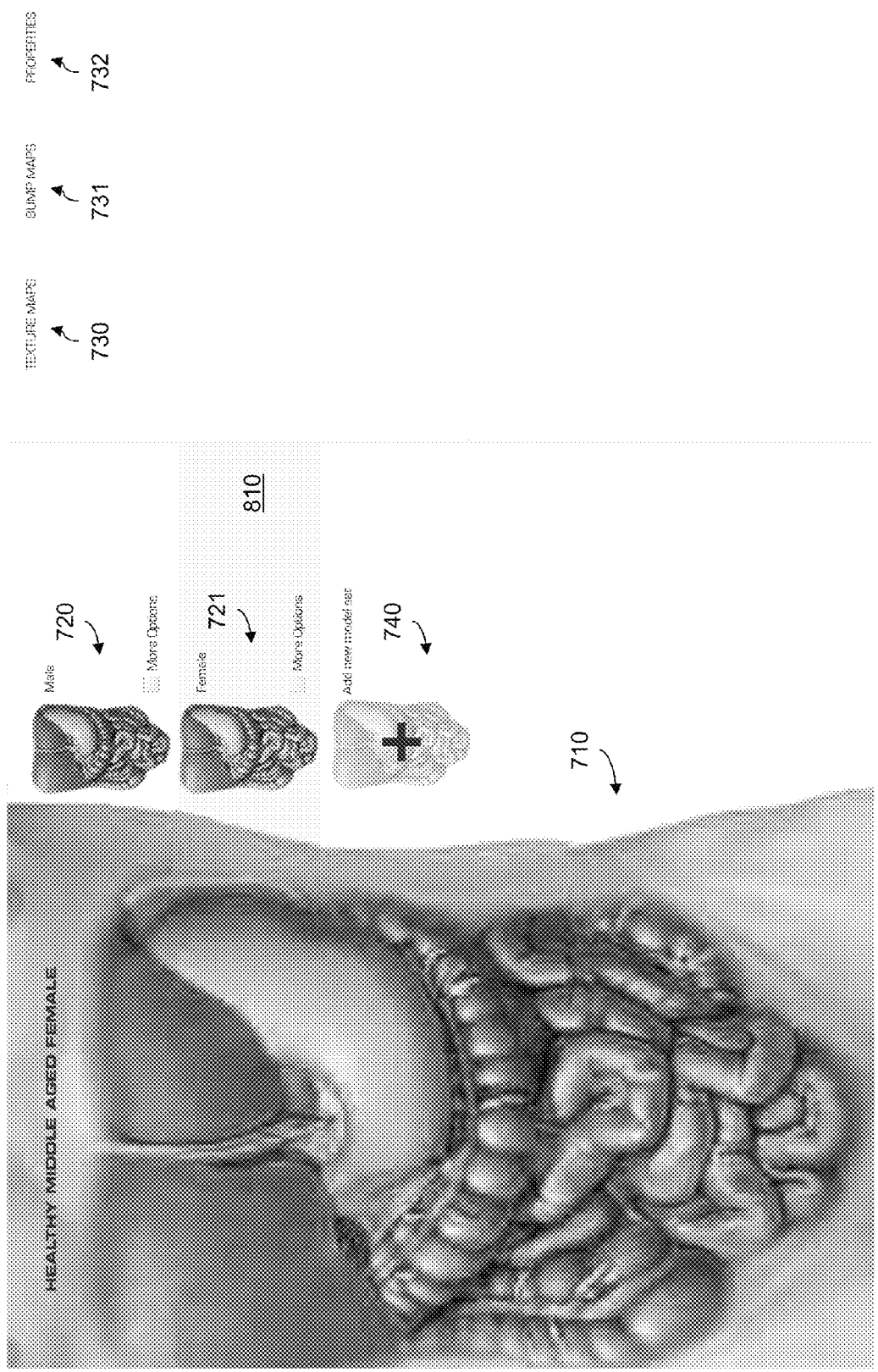

In FIG. 8, the user has identified 810 the patient as a female. After receiving the input from the user, the editor 213 has sent a message to the visualization module 211 to indicate that the patient's sex has been selected. In response, the visualization module changes the shading of the patient's torso 710. The editor 213 re-displays the graphical representation of the patient's torso 710, which provides a more realistic representation of internal organs and tissue. Additionally, the editor 213 activates menus 730-732, which allows a user to affect the graphical representation of the patient. The functionality provided by these menus 730-732 will be described in more detail below.

Figure 9:
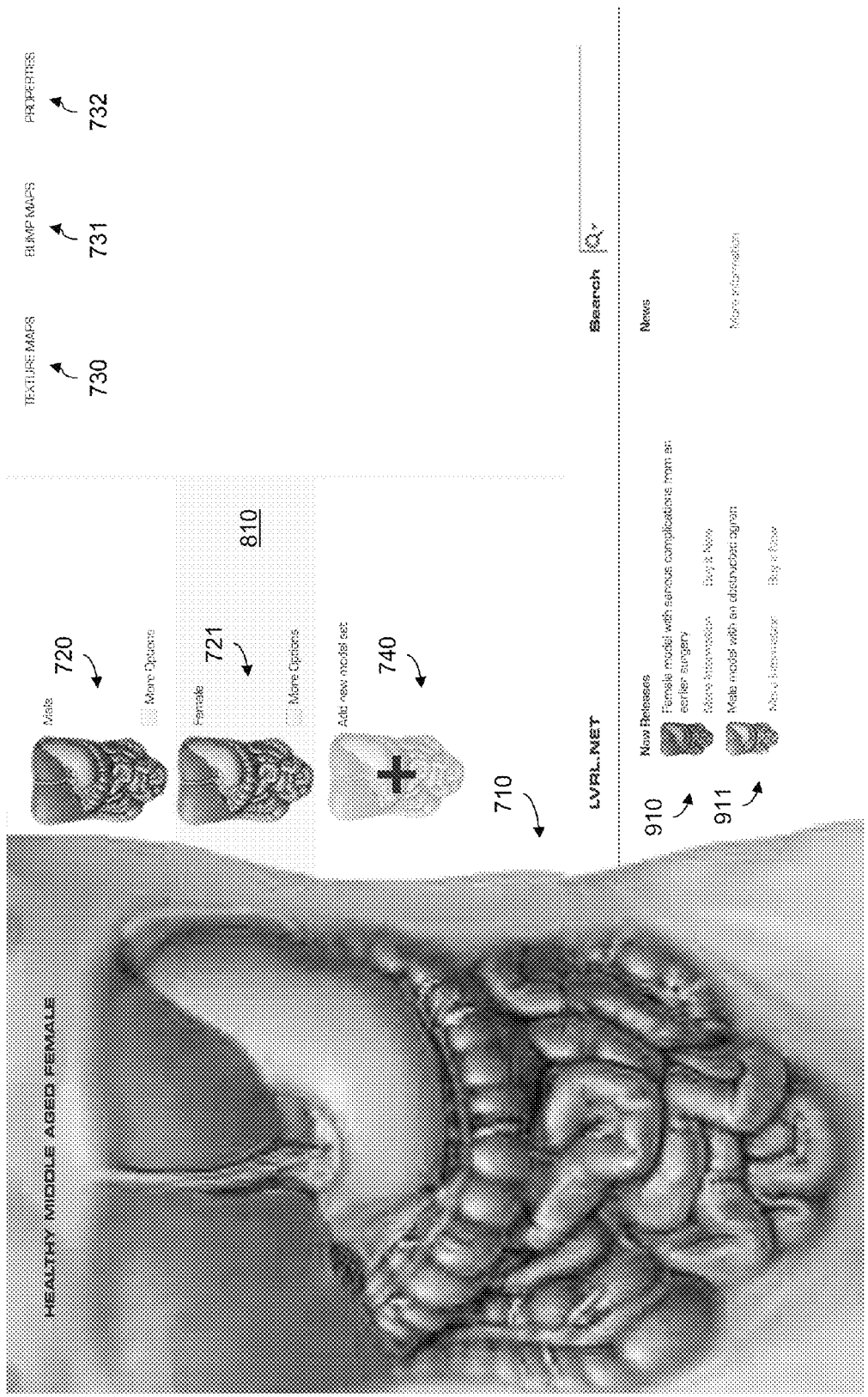

FIG. 9 shows an additional feature of an editor for a medical procedure simulation according to one embodiment of the present invention. In the embodiment shown in FIG. 7, additional templates 910, 911 are available to be imported from a different server. For example, in the embodiment shown in FIG. 7, the user has opted to search templates available on a website. Two models 910, 911 are available for importing, including a female patient model that has been customized to include serious complications from a previous surgery 910. In such an embodiment, a user may select a template that is available from a remote computer to be imported. In one embodiment, a user may enter login information to access a repository of medical procedure simulations hosted by a third-party. In addition, the third-party may require the user to purchase data prior to downloading and incorporating the desired items. The user may access the repository to retrieve a previously-defined simulation of interest and import the simulation into the editor. In such an embodiment, the editor 213 would cause the data import module 310 to receive the desired simulation and convert the incoming simulation data into a form usable by the system 300.

In addition to allowing the user to identify basic characteristics of a patient, such as the sex of the patient, the system 300 allows the user to further customize additional parameters related to the patient.

Figure 10:
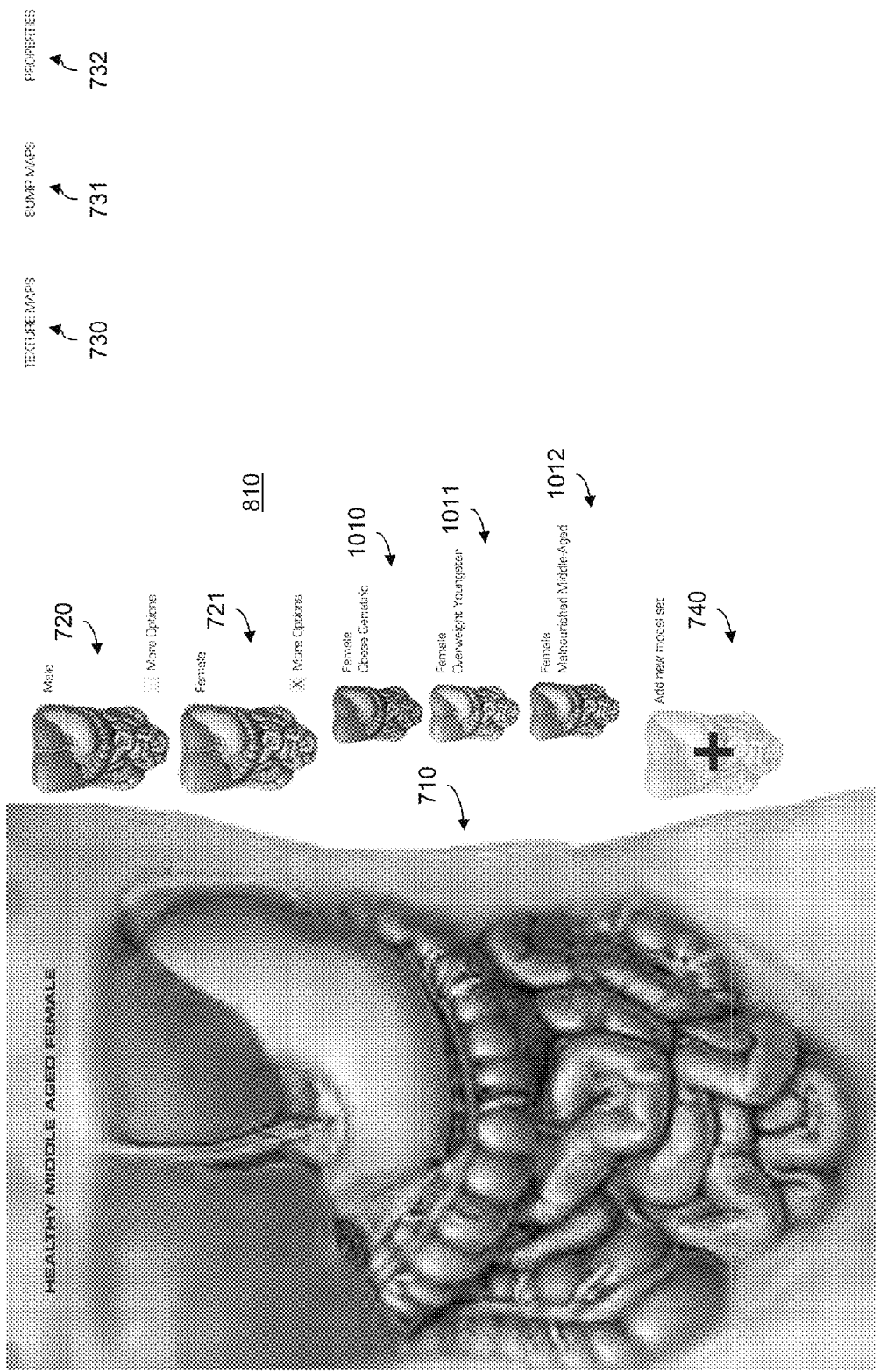

In FIG. 10, a user has indicated that additional parameters should be modified. In the embodiment shown, the user is provided with three basic templates: a female obese geriatric patient 1010, a female overweight young patient 1011, and a female middle-aged malnourished patient 1012. Such templates 1010-1012 may be useful for providing a basic framework that can speed customization of a medical procedure simulation. By using some pre-defined parameters, a user can focus on parameters more relevant to a particular patient, such as anomalies associated with particular internal organs or tissue, or other pathologies.

Figure 11:
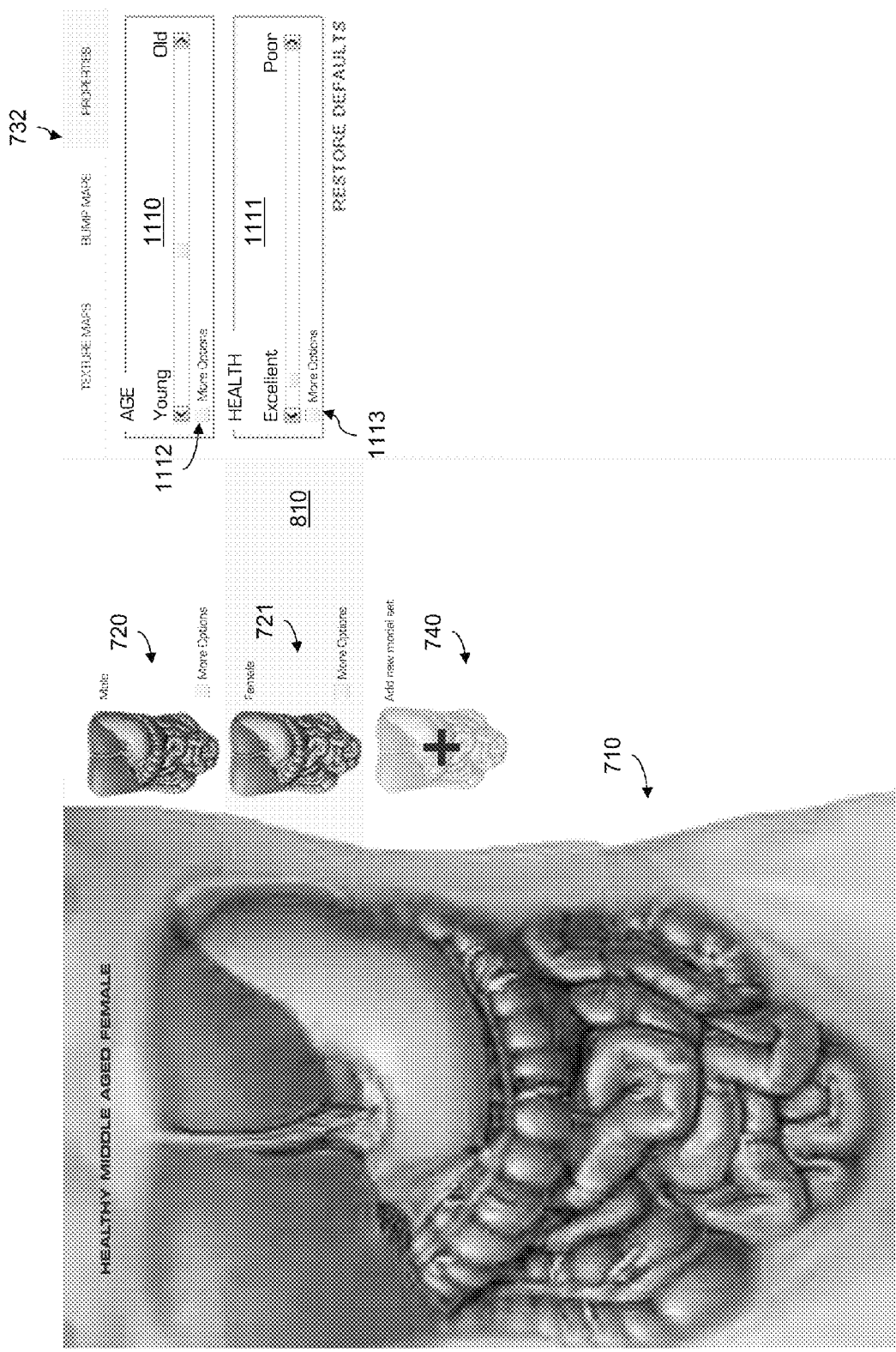

In addition to these basic templates 1010-1012, the system 300 provides the ability to specifically tailor the simulation. As can be seen in FIG. 11, the user has opted to manually specify age and general health characteristics of the patient. The editor 213 provides a slider bar 1110 to allow the user to adjust the age of the patient, and a second slider bar 1111 to allow the user to adjust the health of the patient. In addition to the slider bars 1110, 1111, the editor 213 also provides the option for the user to specify the age or health with greater precision by providing a 'More Options' selection box 1112, 1113. By selecting the appropriate box, the user may precisely specify the patient's age, weight, fat distribution, health conditions, or other characteristics associated with the patient's age or health. For example, in one embodiment, a user may specify a patient's bone density, blood pressure, or cholesterol. In one embodiment, a user may specify other characteristics, such as whether the patient is a smoker, a heavy drinker, or a drug user.

After the patient has used the editor 213 to select the basic characteristics of a patient, the user may customize more specific characteristics of the simulation.

Figure 12:
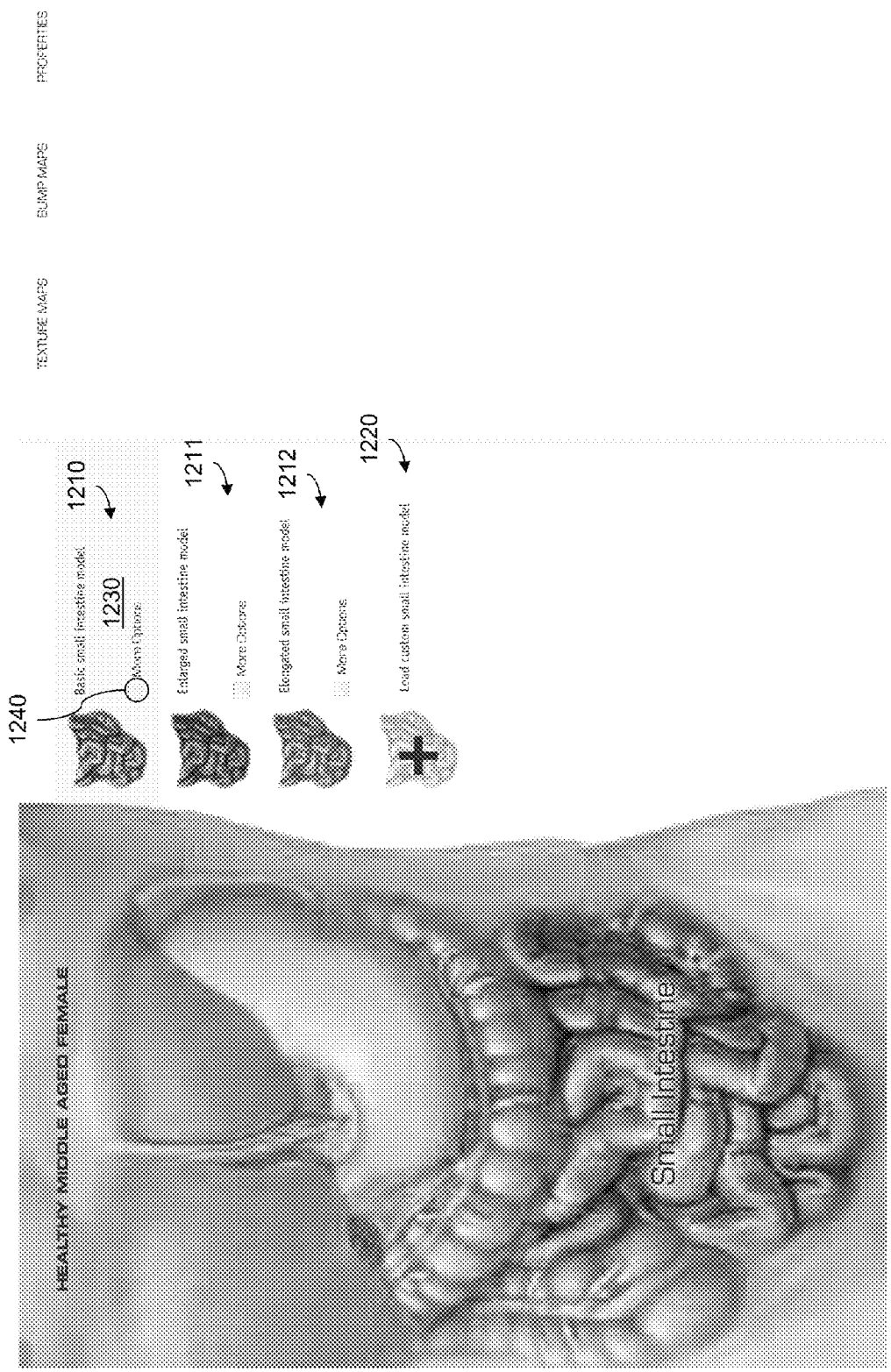

In the embodiment shown in FIG. 12, a user may select from one of three pre-defined templates 1210-1212 describing basic models for the patient's small intestine. Further, the user is given the option of importing a customized small intestine model 1220.

After the user has selected the desired model 1230, the user may select additional options 1240 associated with the selected small intestine model 1230.

Figure 13:
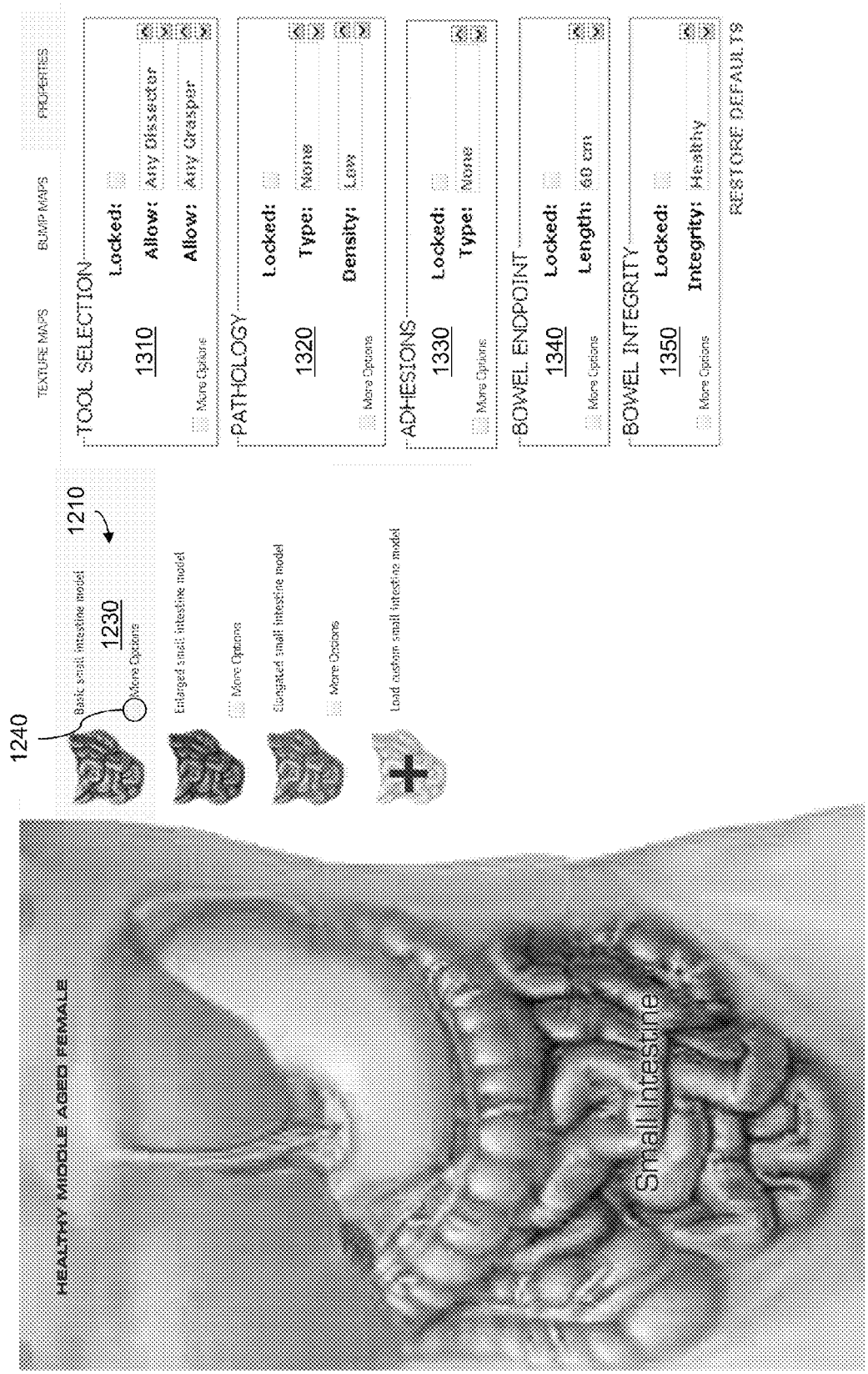

FIG. 13 shows different options available to a user of this embodiment of the system 300. For example, a user may adjust characteristics associated with a pathology 1320, adhesions 1330, bowel endpoints 1340, and bowel integrity 1350. In addition to properties of the small intestine, the user may also identify tools 1310 that may be allowed within the simulation, such as the types of dissector and the types of graspers. Other context-sensitive options may be presented depending on the type of procedure or selected organ. For example, tortuosity may be modified when defining a patient's intestines, or parameters associated with a patient's pregnancy, such as trimester, the number of fetuses, and other parameters.

After the user has completed selecting the physical characteristics of the patient and the area of interest—the small intestines in this embodiment—the user may select parameters associated with the surgical procedure.

Figure 14:
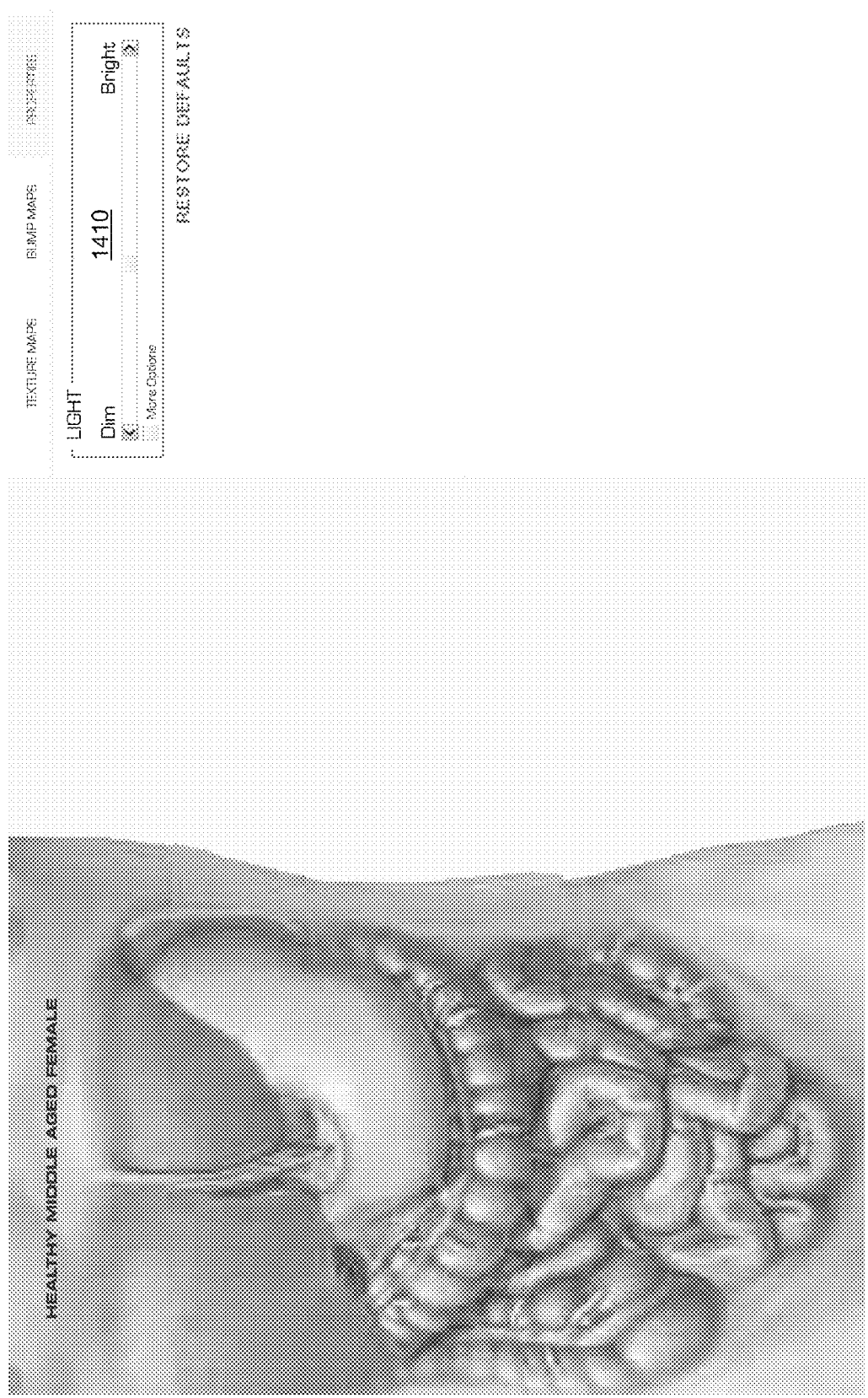

For example, in FIG. 14, the user may customize lighting conditions 1410 for the surgery by adjusting a slider bar between "light" and "dim" settings. As with many parameters, the user may further customize the lighting conditions by selecting the 'More Options' box. For example, in one embodiment, a user may select a rendering quality option to allow a less powerful computer to execute the simulation. In one embodiment, a user may select a viewing angle of a laparoscope, such as 0, 30, or 45 degrees.

The user may next select surgical sites and tools for a user of the simulation. In the embodiment shown in FIG. 15, the user may identify and locate a tool insertion point as well as the type or types of tools 1510-1513 that may be used. As may be seen in FIG. 15, the user has identified a tool insertion point 1520 in the patient's lower right abdomen. In addition, the user is given the option to add an additional trocar site 1610 to the simulation, as may be seen in FIG. 16. Or the user may select and drag a trocar site to a new location using an input device.

The user may also select from the tools 1510-1513 provided within the system 300. By selecting one or more tools, the user may require the simulation to employ only the tools selected. Alternatively, the simulation may allow a simulation user to select the tools to be used, but provide feedback to the user if tools other than those selected in the editor were chosen for use in the simulation. For example, the simulation may inform the simulation user that non-ideal tools were selected, or may reduce the simulation user's score for performing the simulated medical procedure.

In the embodiment shown in FIG. 15, the system 300 has 4 types of tools 1510-1513 available. In addition to the tools that are provided by the system 300, additional tools may be imported from other sources 1530-1532. For example, FIG. 15 shows three additional tools 1510-1513 available for importing into the simulation. The tools 1510-1513 are available through a remote server. The tools 1510-1513 include newly released tools, as well as experimental tools that may be tested within the simulation. In some embodiments, the user may need to pay for tools to be imported. For example, a new, patented tool may be created by a manufacturer for use within a simulator, but require a fee to be paid in order to use the tool. The ability to purchase simulated surgical tools may be incorporated into the system to allow the user to purchase the tool without launching an alternate application, such as a web browser Tools available from other sources may be imported into the system 300. To do so, the system 300 invokes the data import module 310 to import the tool into the simulation To do so, the data import module 310 receives the information from the remote server, for example as a data stream or as a file download, and converts the parameters into a form usable by the system 300. Once a tool has been imported, it may be incorporated into the simulation or made available as a tool option to a user of the simulation.

Figure 17:
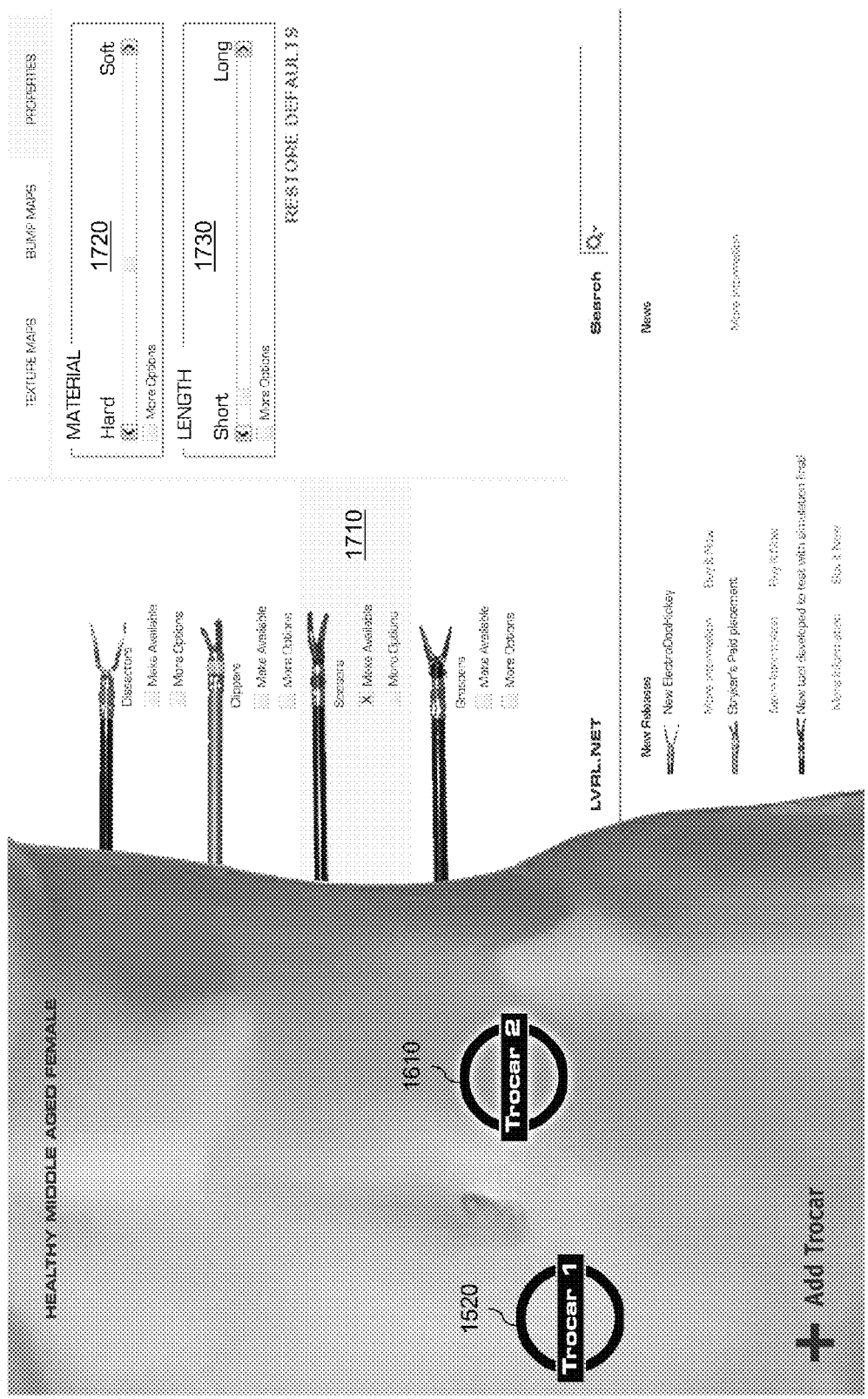
Figure 18:
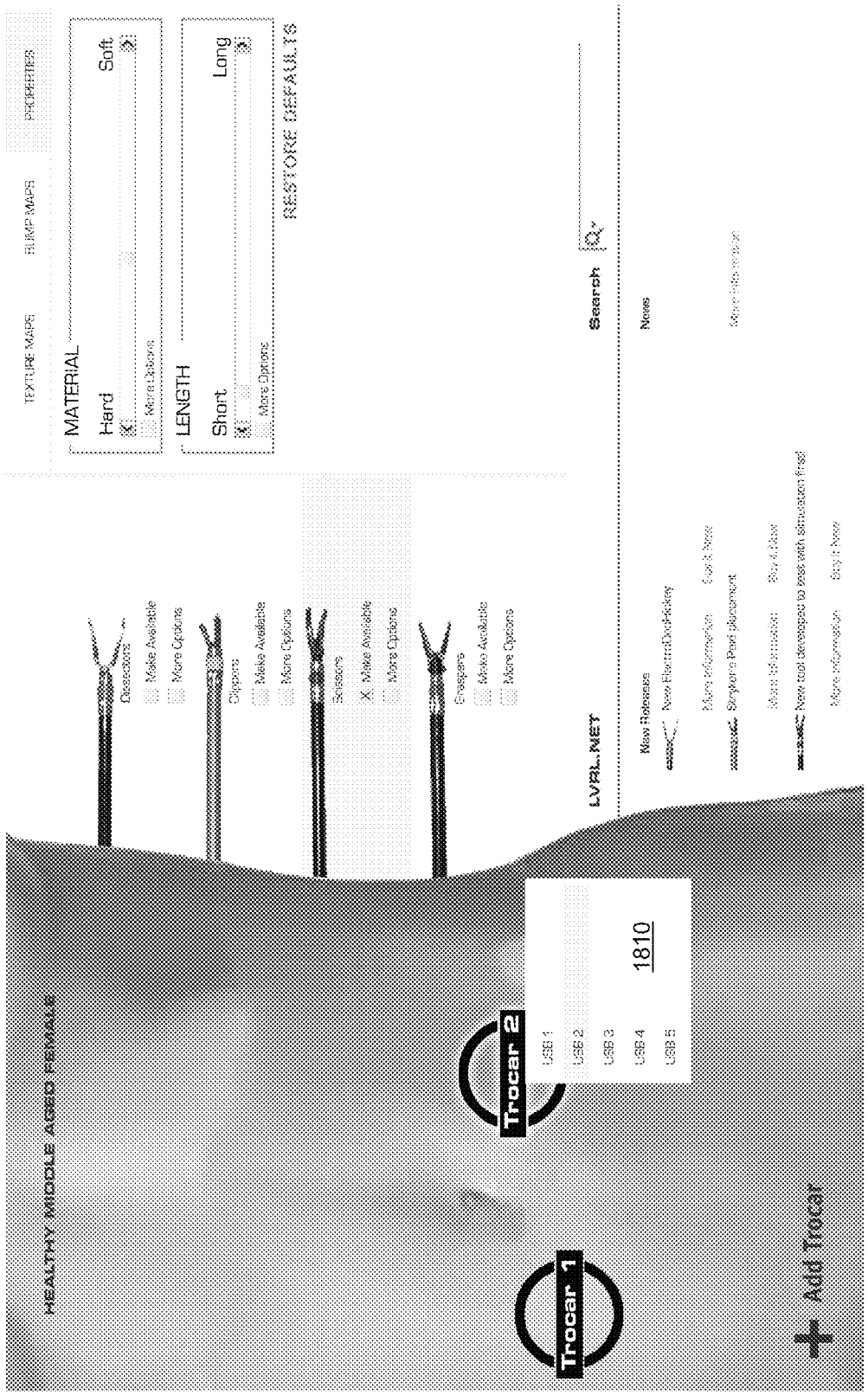

FIG. 17 shows additional options a user may select in one embodiment of the present invention. For example, as shown in FIG. 17, the user has elected 1710 to make a scissors tool available. The user then has the options to customize characteristics of the scissors, such as providing cutting blades made of harder or softer materials 1720, or with shorter or longer cutting blades 1730. In one embodiment, a user may select whether the scissors are single or double action, or whether the scissors are curved or straight. In addition to the slider bars, the user may also elect to customize additional options, such as selecting stainless steel cutting blades, or exactly specifying the length of the blades, such as to conform to a particular tool that will be commonly available to a user of the simulation. For example, if a medical student will typically use a scissors tool with 1.5 cm stainless steel blades in a surgery, a user of the system 300 can specify that the scissors tool has those parameters to more closely approximate the conditions a surgeon would encounter in an actual surgical procedure.

In some embodiments of the present invention, a user may import parameters describing a tool directly from the tool itself. For example, in FIG. 18, the user has selected to import 1810 parameters describing a tool from the tool itself. In this embodiment the user has connected a surgical tool to the computer 110 to a Universal Serial Bus (USB) port on the computer. In this case, the user has selected to import data from the tool, which has been connected as USB device 2. In addition, the user can assign a tool to a trocar location. For example, in the embodiment shown in FIG. 2, in addition to importing parameter data from the tool, the user assigns the tool to the 'Trocar 2' location.

Figure 19:
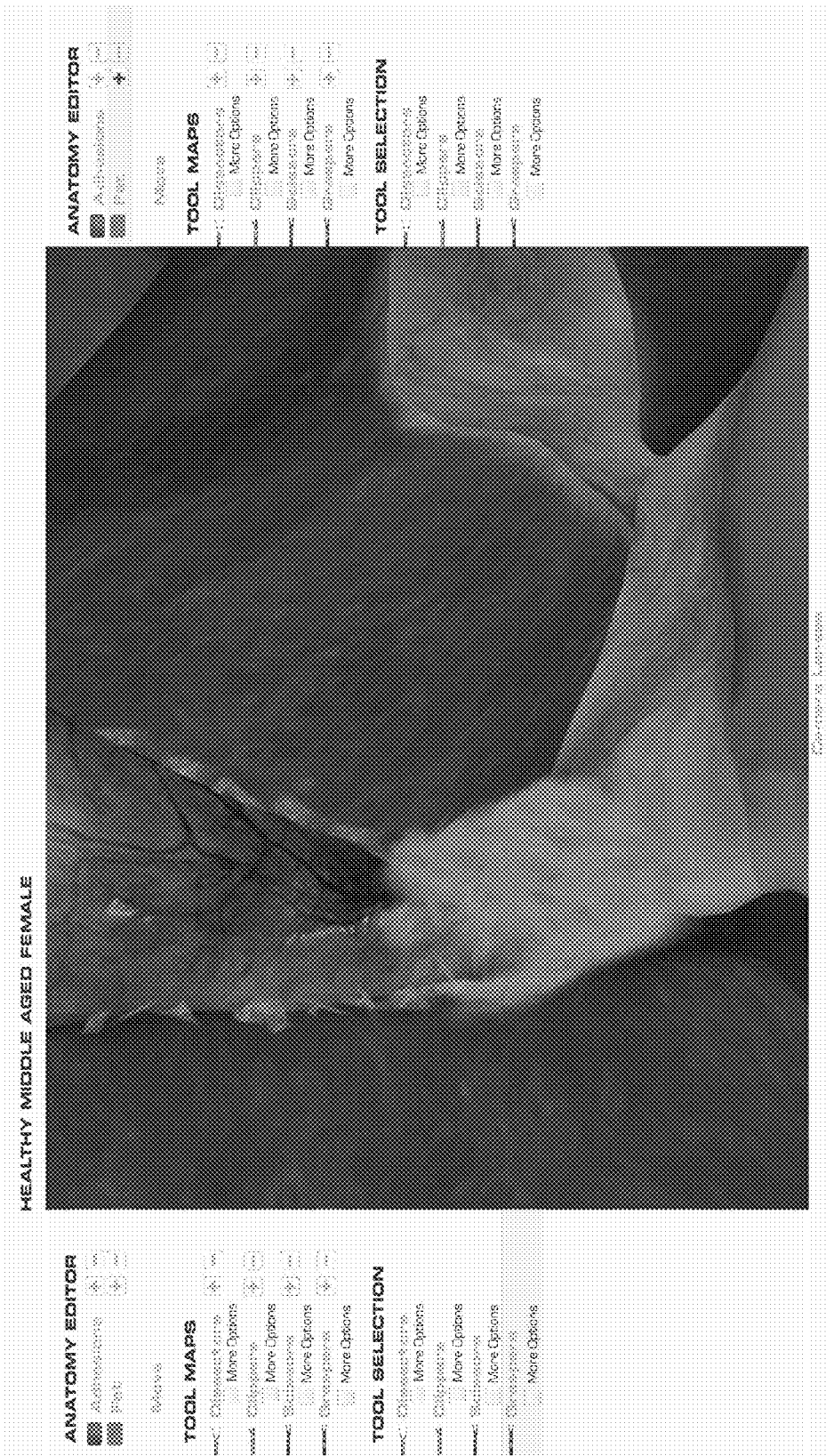
Figure 20:
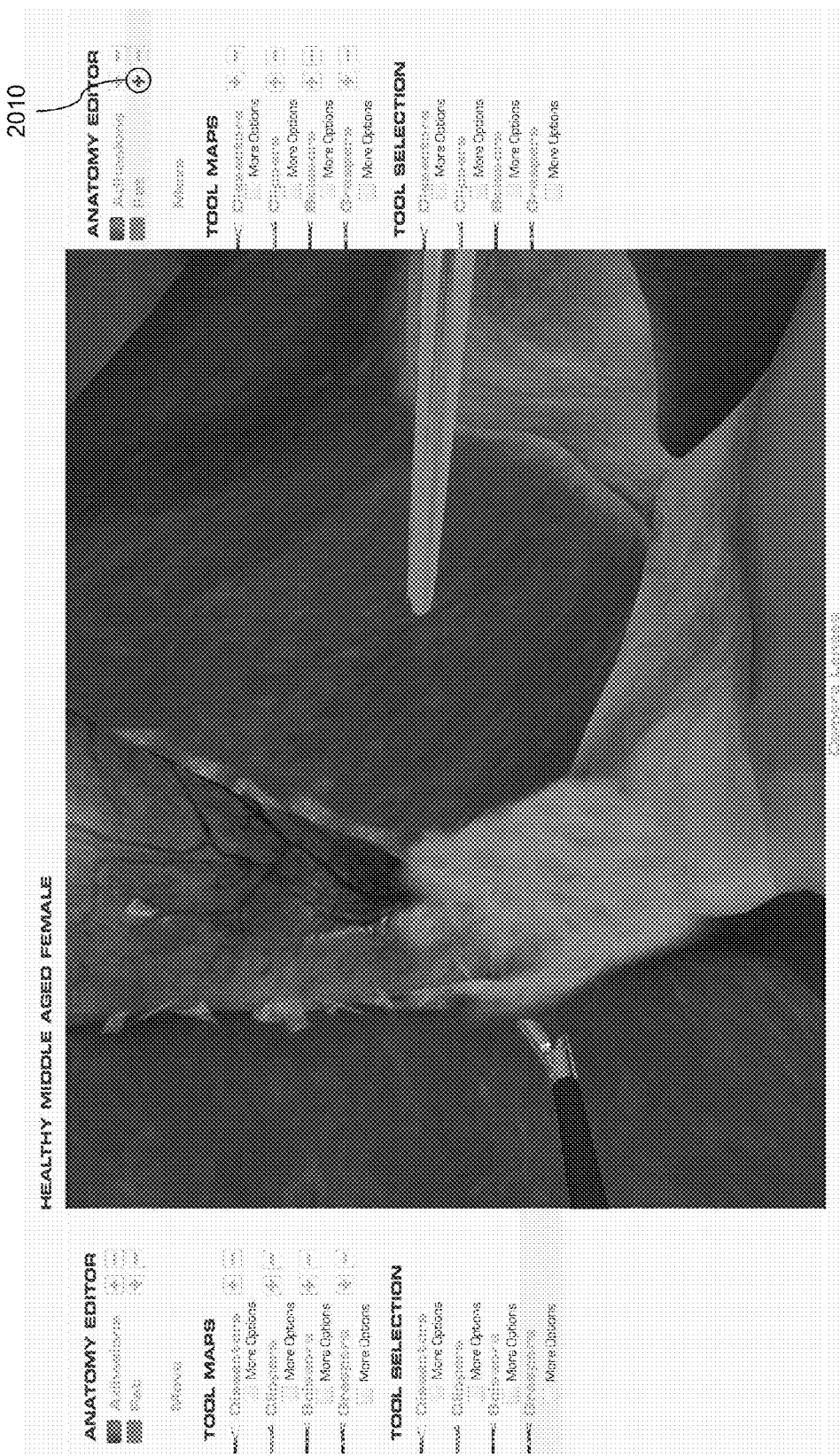
Figure 21:
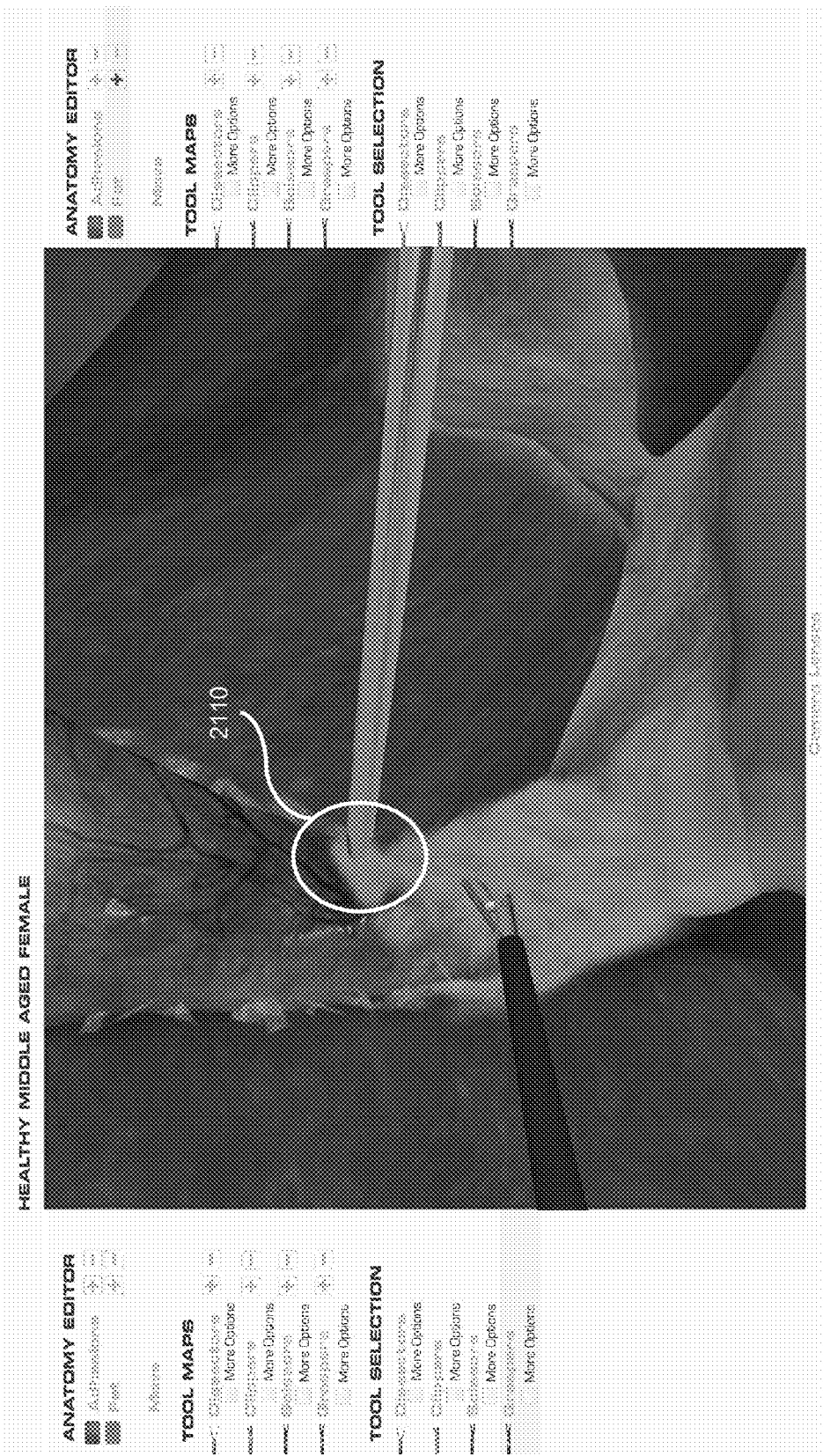

In addition to customizing patient characteristics and tools, a user may customize aspects related to how a user may interact with the patient. For example, FIG. 19 shows an internal view of the patient's abdomen. In this view, the user is given the option of identifying areas where particular tools may be used, and customizing environmental conditions. For example, in FIG. 20, the selected tools may be seen as they may look during a simulation. However, in this view, the user has indicated that fat deposits are to be added. In FIG. 21, the user-added additional fat deposits have been added by the user and will be present during a simulation. In the embodiment shown, the user has added fat deposits by using a paintbrush-like tool. Using such a tool, a user may create different sized and shaped fat deposits. For example, a user may indicate a larger or thicker fat deposit by passing the tool over the same location multiple times.

Figure 22:
Figure 23:
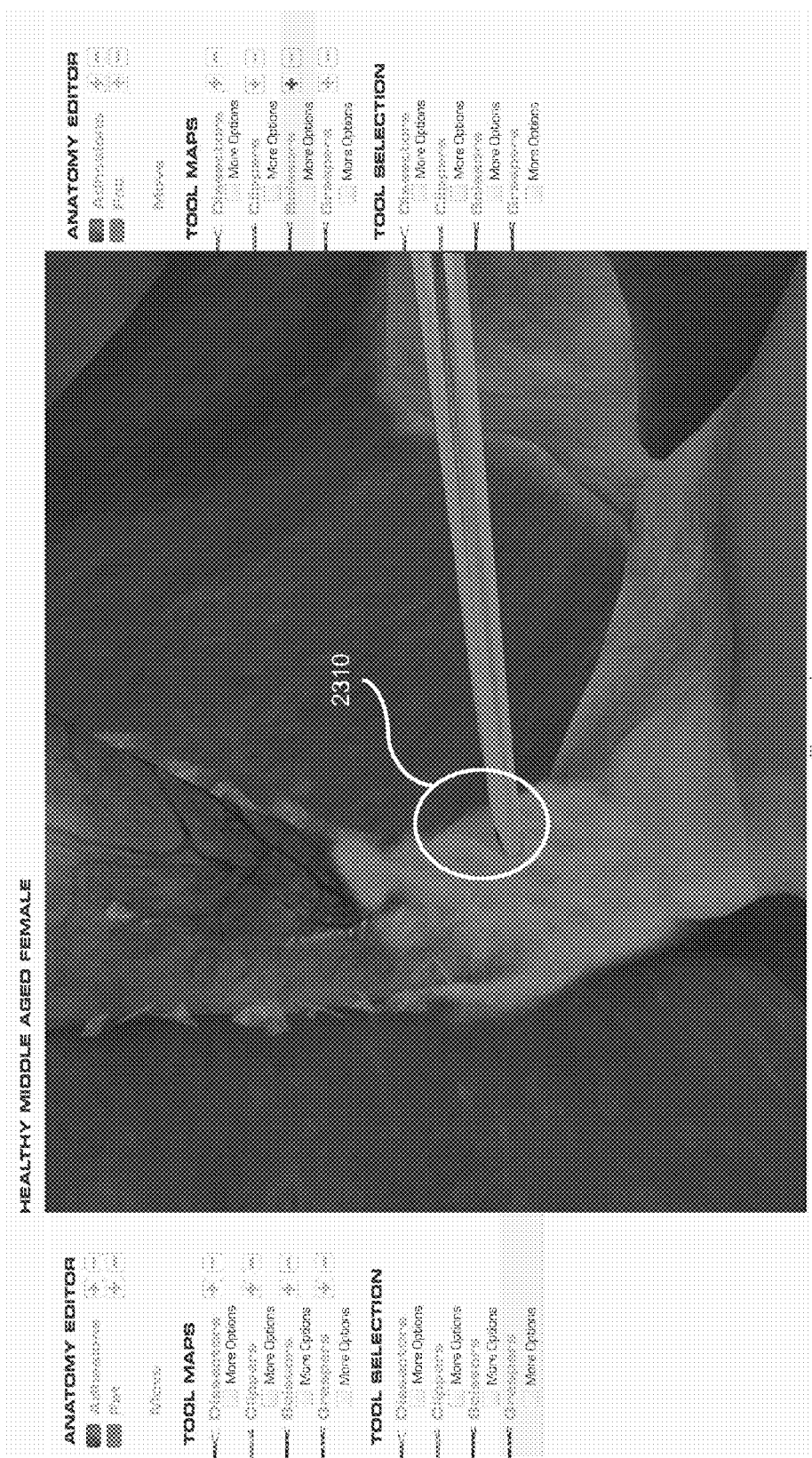

FIGS. 22 and 23 show how a user may employ the system 300 to define where a tool may be used within a simulation. In FIG. 22, the user has selected the option 2210 to identify where within the scene a user may safely employ the scissors tool. And in FIG. 23, the user has identified the area 2310 in which the scissors may be safely used in the simulation. In addition, the user may create a script to provide feedback information to a user and associate the script with the regions where use of the scissors is not allowed. For example, in one embodiment, the user may create a script with textual feedback and associate the script with the region where scissors may not be used. When a user later performs the simulated medical procedure, if the user attempts to use the scissors tool in a disallowed region, the script may be executed and display text for the simulation user to view. For example, the text may indicate that the user attempted to use the scissors in a dangerous region. In one embodiment, the script may reduce the user's score to indicate a mistake during the simulation.

Figure 24:
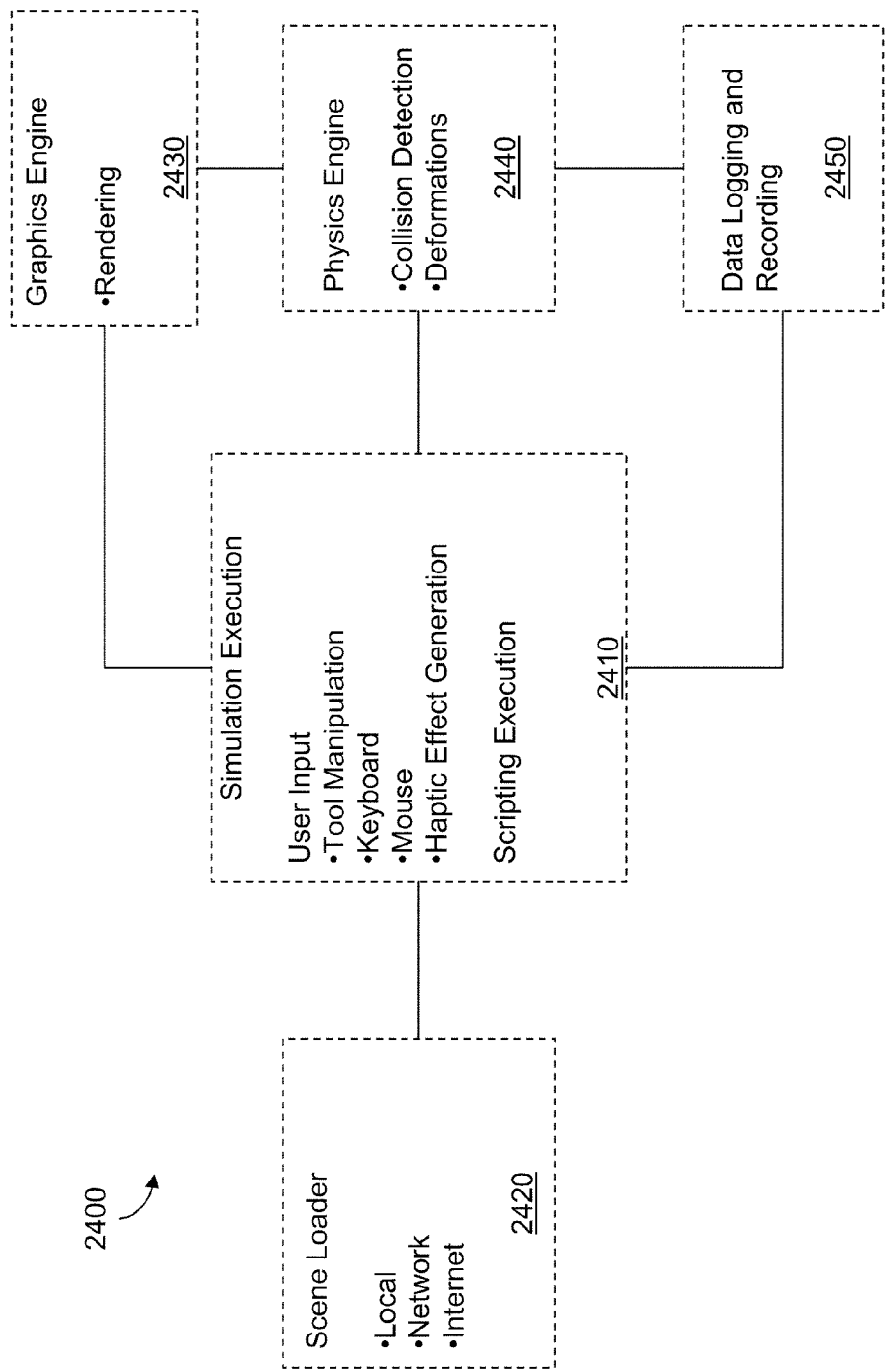
FIG. 24 is a block diagram showing a system for simulating a medical procedure according to one embodiment of the present invention.

Referring now to FIG. 24, FIG. 24 is a block diagram showing a system for simulating a medical procedure according to one embodiment of the present invention. FIG. 24 will be described with reference to the system 100 shown in FIG. 1.

The system 2400 shown in FIG. 24 comprises a simulation execution module 2410, a scene loader 2420, a graphics engine 2430, a physics engine 2440, and a data logging and recording module 2450. The embodiment shown may be executed on a computer system, such as the computer 110 shown in FIG. 1, which comprises a processor 111 and a memory 112. In addition, the computer system also comprises a display 130 and one or more input devices 120.

In the embodiment shown in FIG. 24, the simulation execution module 2410 manages the execution of the system 2400. It loads a scene from a computer-readable medium to be executed. For example, the simulation execution module 2410 may employ the scene loader module 2420 to access a scene stored on a local computer-readable medium, such as a hard drive or other non-volatile memory connected to the computer 110. In another embodiment, the scene loader module may access a computer-readable medium connected to a remote computer, such as a computer connected to a local area network in communication with the computer 110. In a further embodiment, the scene loader module 2420 may access a scene available from a remote computer or system over a wide area network, such as a website that allows the purchase and download of scenes for use with embodiments of the present invention.

Once a scene has been loaded and the simulation begins, the simulation execution module 2410 receives inputs from the user and sends information to other modules too process responses to the inputs. For example, a user may move an input device 120, such as a haptically-enabled input device that has been configured to resemble a surgical tool represented in the simulation, to cause the device to be inserted via a trocar into a surgery site. The execution module 2410 receives input signals from the input device 120 and determines a movement of a simulated surgical tool based at least in part on the input signals.

In one embodiment, the execution module 2410 also generates haptic effects to be output to one or more user input devices, such as simulation surgical tools. In some embodiments, a simulation surgical tool may comprise one or more actuators configured to provide haptic feedback to a user. For example, in one embodiment, a simulation surgical tool may simulate a laparoscopic surgical tool. Such a simulation surgical tool may comprise an actuator configured to provide haptic effects associated with opening and closing grips on the tool. Embodiments of such a tool may be found in co-pending U.S. patent application Ser. No. 10/196,717, filed Jul. 15, 2002 and entitled "Pivotable Computer Interface," the entirety of which is incorporated herein by reference. Still other haptically-enabled simulation surgical tools may be employed, such as catheters and others.

Haptic effects to be output to a user of one or more embodiments may comprise active or passive haptic effects. For example, in one embodiment a simulation of a medical procedure may require a user to insert a catheter into a patient. In such an embodiment, the embodiment may output resistive haptic effects to the user to simulate the feel of a catheter sliding through tissue within the patient. Additionally, the embodiment may output a vibrational haptic effect to the user. For example, in one embodiment, a system 2400 may output a vibration to a user to indicate the user has made an error during performance of the procedure. In such an embodiment, a script may comprise programming to output a haptic effect, such as a vibration, upon the occurrence of an error. In addition to the vibration, a message may be displayed to the user or an audible sound may be output to indicate the error.

In haptically-enabled embodiments, suitable actuators may be incorporated into simulation surgical tools to output the haptic effects. Such actuators may comprise passive actuators or active actuators. For example, in one embodiment, a vibrational haptic effect may be generated by an eccentric rotating mass (ERM) actuator or by a linear resonant actuator (LRA). In one embodiment, a braking effect may be generated by bringing a braking surface into contact with the simulation surgical tool, such as with an electromagnetic force or with a motor. Still other types of actuators may be employed in various embodiments to provide desired haptic effects.

After determining the movement of the simulated surgical tool, the simulation execution module 2410 transmits information to the physics engine 2440 to determine whether contact with other objects in the scene has occurred. The physics engine 2440 will be described in more detail below. In addition, the simulation execution module 2410 also transmits information to the graphics engine 2430 to update a view of the simulation based on the newly-determined position of the simulated surgical tool.

In the embodiment shown in FIG. 24, the physics engine 2440 is configured to detect collisions between objects in the scene, and to determine deformations of objects in the scene. The physics engine may determine collisions between two objects in the scene, such as two internal organs contacting each other, or a surgical tool contacting an object within the scene. The physics engine 2440 may determine a contact by determining whether a point on a first object contacts or passes through a plane segment defined by three or more points on a triangular mesh describing a second object, or other suitable method.

The physics engine 2440 also determines deformations of objects in the scene. For example, the physics engine 2440 may determine deformations resulting from contact between two objects, or as the result of one object changing shape due to, for example, a biological or physiological process (e.g. a heart beating). A deformation of an object may be determined based on physical characteristics of the model, such as a resilience of edges within a wire mesh describing the object to changes in length or orientation. For example, a surgical tool may be pressed against an object within a patient. The physics engine may analyze characteristics of the object within a distance of a point of contact on the object, such as within 2 cm. The physics engine calculates a pressure on the object based on the movement of the surgical tool, and calculates a movement of one or more vertices within the object's model based on the pressure and a stiffness characteristic associated with edges connecting the vertices. In addition, the simulation engine may transmit information to the simulation execution module 2410 to indicate a collision. Such information may be employed by the simulation module 2410 to generate haptic, visual, or audio feedback to a user.

In the embodiment shown in FIG. 24, the system 2400 further comprises a data logging and recording module 2450. In one embodiment of the present invention, the system 2400 is configured to log a user's movement of surgical tools used within a simulation. The data logging and recording module 2450 receives signals from the simulation execution module 2410 indication the position and orientation of a surgical tool each time either the position or the orientation of the surgical tool changes. The data logging and recording module 2450 stores each received position and orientation of the surgical tool after being received from the simulation execution module 2410. By logging each change of position and orientation, the system 2400 may allow a user to replay the execution of a surgical procedure based on the logged position and orientation information. Such a replay may allow an instructor to review the performance of the surgery with the student, such as by allowing the instructor to pause the replay and change the viewpoint of the replay to provide advice or feedback to the student.

Figure 25:
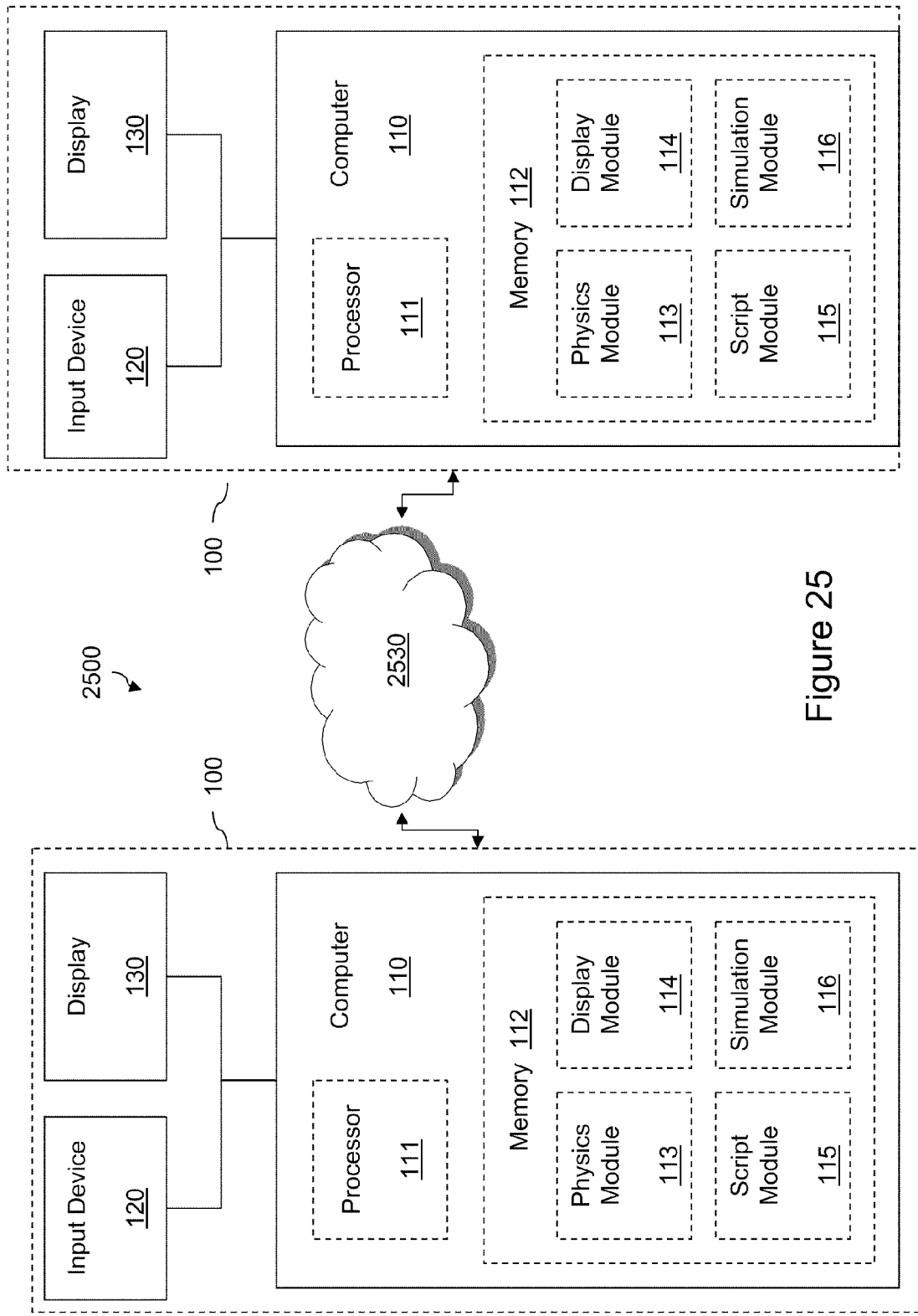
FIG. 25 is a block diagram showing a system for simulating a medical procedure according to one embodiment of the present invention.

Referring now to FIG. 25, FIG. 25 shows a block diagram showing a system 2500 for simulating a medical procedure according to one embodiment of the present invention. In the embodiment shown in FIG. 25, two systems 100 for simulating a medical procedure according to one embodiment of the present invention are in communication with each other via a network 2530. The systems 100 each comprise a system 100 shown in FIG. 1. In addition, each system is configured to communicate with the network 2530 and other systems 100. In such an embodiment, users of the systems 100 may perform a medical procedure in a cooperative manner, with one user performing one portion of the medical procedure, while a second user performs another portion of the medical procedure. For example, one user may be responsible for creating incisions and inserting tools, while the second user may then use the tools. In another embodiment, each user may perform their respective portion of the simulation substantially simultaneously such that each user may interact with the other during the simulation. For example, one user may manipulate a grasping tool, while the second user manipulates a cutting tool, such as a scissors tool. Such an embodiment may more accurately represent more complex medical procedures that involve multiple practitioners. Alternatively, such an embodiment may allow a more junior user to work with a more senior user to both observe the senior user, but also participate in the procedure as well.

While the methods and systems herein are described in terms of software executing on various machines, the methods and systems may also be implemented as specifically-configured hardware, such a field-programmable gate array (FPGA) specifically to execute the various methods. For example, referring again to FIGS. 1 and 24, embodiments can be implemented in digital electronic circuitry, or in computer hardware, firmware, software, or in combination of them. In one embodiment, a computer may comprise a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

General

The foregoing description of some embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

That which is claimed is:

1. A system for simulating a medical procedure comprising:
an editor configured to allow a user to customize one or more characteristics of a scene, the scene providing a definition for a customized simulation of a medical procedure;
a physics module configured to model at least one physical property of a user-defined model of an organic object associated with a patient, the scene comprising the user-defined model of the organic object;
a display module configured to cause a display of the scene comprising the user-defined model of the organic object;
a script module configured to:
execute a user-defined medical procedure script associated with the scene, the user-defined medical procedure script comprising user-defined program code,
determine one or more haptic effects based on the user-defined medical procedure script, and
determine a visual prompt based on the user-defined medical procedure script;
a simulation module in communication with the physics module, the display module, and the script module, the simulation module configured to:
receive input from a simulated medical apparatus; and
execute the customized simulation of the medical procedure based at least in part on the scene, the user-defined model of the organic object, and the user-defined program code of the user-defined medical procedure script, the simulation module configured to cause the one or more haptic effects to be generated and the visual prompt to be displayed based upon the occurrence of a scripted event or the received input.

2. The system of claim 1, wherein the user-defined model of the organic object comprises at least one parameter associated with at least one of an age of the patient, a sex of the patient, a weight of the patient, a level of health of the patient, a pathology, or adhesion information.

3. The system of claim 1, wherein the user-defined medical procedure script comprises at least one of prompt information, textual information, scoring information, timing information, lighting information, texture information, surgical site information, or surgical tool information.

4. The system of claim 1, wherein the at least one physical property of the user defined-model of the organic object comprises a density, an elasticity, or a thickness.

5. The system of claim 1, wherein the simulation module is in communication with a simulation input device and is configured to receive an input signal from the simulation input device.

6. The system of claim 5, wherein the simulation input device comprises an actuator configured to output a haptic effect to the simulation input device.

7. The system of claim 6, wherein the simulation input device comprises a laparoscopy simulation device.

8. The system of claim 1, further comprising a data logging and recording module configured to:
receive a logging signal comprising a position and an orientation of the simulated medical apparatus; and
store the position and the orientation.

9. The system of claim 8, wherein the data logging and recording module is further configured to transmit a replay signal comprising a stored position and a stored orientation of the simulated medical apparatus.

10. A computer-implemented method for simulating a medical procedure comprising:
receiving, by a processor, a user-defined scene comprising:
a model of a user-defined organic object associated with a patient, the model of the user-defined organic object comprising at least one physical property,
a description of a surgical tool, and
a user-defined medical procedure script comprising user-defined program code;
receiving customizations to the user-defined scene from an editor configured to allow a user to customize one or more characteristics of the user-defined scene, the user-defined scene providing a definition for a customized simulation of a medical procedure;
determining one or more haptic effects based on the user-defined medical procedure script, determining a visual prompt based on the user-defined medical procedure script, executing, by a processor, the customized simulation of the medical procedure based at least in part on the user-defined organic object and the user-defined program code of the user-defined medical procedure script, the simulation configured to cause the haptic effect to be generated and the visual prompt to be displayed upon the occurrence of the scripted event; and outputting, by a processor, an image of the user-defined organic object based at least in part on the simulation.

11. The computer-implemented method of claim 10, wherein the model of the user-defined organic object comprises at least one parameter associated with at least one of an age of the patient, a sex of the patient, a weight of the patient, a level of health of the patient, a pathology, or adhesion information.

12. The computer-implemented method of claim 10, wherein the user-defined medical procedure script comprises at least one of prompt information, textual information, scoring information, timing information, lighting information, surgical site information, or surgical tool information.

13. The computer-implemented method of claim 10, further comprising receiving an input signal from a simulation input device.

14. The computer-implemented method of claim 11, further comprising transmitting an actuator signal to an actuator in communication with the simulation input device, the actuator signal configured to cause the actuator to output a haptic effect on the simulation input device.

15. The computer-implemented method of claim 14, wherein the simulation input device comprises a laparoscopy simulation device.

16. A non-transitory computer-readable medium comprising program code, the program code comprising:
   program code for receiving a model of a user-defined organic object associated with a patient, the user-defined organic object comprising at least one physical property;
   program code for receiving a user-defined medical procedure script, the user-defined medical procedure script comprising user-defined program code;
   program code for receiving customizations to a user-defined scene from an editor configured to allow a user to customize one or more characteristics of the user-defined scene, the scene providing a definition for a customized simulation of a medical procedure and associated with the user-defined organic object and the user-defined medical procedure script;
   program code for determining one or more haptic effects based on the user-defined medical procedure script,
   program code for determining a visual prompt based on the user-defined medical procedure script;
   program code for executing the customized simulation of the medical procedure based at least in part on the scene, the model of the user-defined organic object, and the user-defined program code of the user-defined medical procedure script, the simulation configured to cause the haptic effect to be generated and the visual prompt to be displayed based upon the occurrence of the scripted event; and
   program code for outputting an image of the model of the user-defined organic object based at least in part on the simulation.

17. The non-transitory computer-readable medium of claim 16, wherein the model of the user-defined organic object comprises at least one parameter associated with at least one of an age of the patient, a sex of the patient, a weight of the patient, a level of health of the patient, a pathology, or adhesion information.

18. The non-transitory computer-readable medium of claim 16, wherein the user-defined medical procedure script comprises at least one of prompt information, textual information, scoring information, timing information, lighting information, surgical site information, or surgical tool information.

19. The non-transitory computer-readable medium of claim 16, further comprising receiving an input signal from a simulation input device.

20. The non-transitory computer-readable medium of claim 17, further comprising transmitting an actuator signal to an actuator in communication with the simulation input device, the actuator signal configured to cause the actuator to output a haptic effect on the simulation input device.

21. The non-transitory computer-readable medium of claim 20, wherein the simulation input device comprises a laparoscopy simulation device.

22. A system, comprising:
   a processor; and
   a non-transitory computer-readable medium in communication with the processor, the computer readable medium comprising:
      a data import module configured to receive information describing at least one of a simulation of a medical procedure, a model of an organic object, a model of a surgical tool, or a medical procedure script,
      a visualization module configured to generate a visualization signal configured to cause a display of a view of the model of the organic object,
      an editor module configured to:
         receive the information from the data import module,
         generate a patient template for a patient,
         receive a customization of a characteristic of the patient,
         receive a customization of a pathology,
         receive a customization of a surgical tool,
         receive and edit the medical procedure script to create a user-defined medical procedure script for the customized simulation, the editor module capable of including user-defined program code in the user-defined medical procedure script, the user-defined program code comprising at least one command to provide a haptic effect and a visual prompt based on an occurrence of a scripted event;
         transmit a signal to the visualization module comprising the characteristic of the patient and the pathology, and
         transmit a signal to the scene generation module comprising the characteristic of the patient, the user-defined script, and the pathology;
      a scene generation module configured to receive the customization of the characteristic of the patient, the user-defined script, and the customization of the pathology, and to generate a customized scene having a customized simulation of a medical procedure based on the customization of the characteristic of the patient, the customization of the pathology, the customization of the surgical tool, and the user-defined medical procedure script.

23. The system of claim 22, wherein the characteristic of the patient comprises at least one of an age of the patient, a sex of the patient, a weight of the patient, a level of health of the patient, a skin color, smoking information, a pathology, or adhesion information.

24. The system of claim 22, wherein the editor module is further configured to receive a customization of an environmental parameter associated with the customized simulation.

25. The system of claim 24, wherein the environmental parameter comprises one of a lighting parameter, an adhesion location, or a fatty tissue location.

26. The system of claim 22, wherein the view is a three-dimensional interior view of a patient.

27. The system of claim 26, wherein the view simulates a perspective of a surgeon performing the customized medical procedure.

28. The system of claim 22, wherein the scene generation module is further configured to generate a signal comprising a customized organic object.

29. The system of claim 28, wherein the customized organic object comprises an internal organ.

30. The system of claim 22, wherein the data import module is configured to receive the information from a remote server.

31. The system of claim 30, wherein the data import module is configured to import the information into the customized simulation of the medical procedure and the modification comprises at least one of an age of the patient, a sex of the patient, a weight of the patient, a level of health of the patient, a pathology, or adhesion information.

32. The system of claim 31, wherein the data import module is configured to receive the information from multiple remote servers and to integrate the information.

33. The system of claim 31, wherein the data import module is configured to upload the information to a remote server for distribution or use by other users.

34. The system of claim 22, wherein the scene generation module is configured to upload the customized simulation to a remote server for distribution or use by other users.

35. The system of claim 1, wherein one of the one or more characteristics of the scene comprises the user-defined medical procedure script, and wherein the editor is configured to allow editing of the user-defined medical procedure script.

\* \* \* \* \*